US008759544B2

(12) United States Patent
Evans et al.

(10) Patent No.: US 8,759,544 B2
(45) Date of Patent: Jun. 24, 2014

(54) SYNTHESIS OF AN ANTIVIRAL COMPOUND

(71) Applicant: Gilead Sciences, Inc., Foster City, CA (US)

(72) Inventors: Jared Wayne Evans, Belmont, CA (US); Shinji Fujimori, San Francisco, CA (US); Grace M. Huynh, San Francisco, CA (US); Qi Liu, Union City, CA (US); Martin Gerald Teresk, San Jose, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/801,039

(22) Filed: Mar. 13, 2013

(65) Prior Publication Data

US 2014/0051867 A1 Feb. 20, 2014

Related U.S. Application Data

(60) Provisional application No. 61/684,543, filed on Aug. 17, 2012.

(51) Int. Cl.
C07D 409/00 (2006.01)
C07D 409/12 (2006.01)

(52) U.S. Cl.
USPC .......................................................... 549/60

(58) Field of Classification Search
USPC .......................................................... 549/60
See application file for complete search history.

(56) References Cited

U.S. PATENT DOCUMENTS

| | | | |
|---|---|---|---|
| 5,861,421 | A | 1/1999 | Christensen, IV et al. |
| 6,881,741 | B2 | 4/2005 | Chan Chun Kong et al. |
| 6,887,877 | B2 | 5/2005 | Chan Chun Kong et al. |
| 7,402,608 | B2 | 7/2008 | Chan Chun Kong et al. |
| 7,521,473 | B2 | 4/2009 | Lee et al. |
| 7,569,600 | B2 | 8/2009 | Denis et al. |
| 2002/0002199 | A1 | 1/2002 | Jeppesen et al. |
| 2003/0229053 | A1 | 12/2003 | Chan Chun Kong et al. |
| 2004/0116509 | A1 | 6/2004 | Chan Chun Kong et al. |
| 2005/0119332 | A1 | 6/2005 | Jeppesen et al. |
| 2006/0142347 | A1 | 6/2006 | Chan Chun Kong et al. |
| 2006/0276533 | A1 | 12/2006 | Denis et al. |
| 2007/0099929 | A1 | 5/2007 | Thede et al. |
| 2008/0299080 | A1 | 12/2008 | Chan Chun Kong et al. |
| 2009/0274655 | A1 | 11/2009 | Grimes et al. |
| 2011/0020278 | A1 | 1/2011 | Canales et al. |
| 2011/0178058 | A1 | 7/2011 | Canales et al. |
| 2011/0178129 | A1 | 7/2011 | Canales et al. |
| 2013/0052161 | A1 | 2/2013 | Watkins |

FOREIGN PATENT DOCUMENTS

| | | |
|---|---|---|
| WO | 02/100846 A1 | 12/2002 |
| WO | 02/100851 A2 | 12/2002 |
| WO | 2004/052885 | 6/2004 |
| WO | 2005/095386 A1 | 10/2005 |
| WO | 2006/072347 A2 | 7/2006 |
| WO | 2006/072348 | 7/2006 |
| WO | 2007/093365 A2 | 8/2007 |
| WO | 2008/058393 A1 | 5/2008 |
| WO | 2010/065668 | 6/2010 |
| WO | 2011/011303 | 1/2011 |
| WO | 2011/031669 | 3/2011 |
| WO | 2011/068715 | 6/2011 |
| WO | WO 2011/088345 A1 | 7/2011 |
| WO | 2012/006055 | 1/2012 |
| WO | WO 2012/087596 A1 | 6/2012 |

OTHER PUBLICATIONS

Boyer, N, et al. (2000) "Pathogenesis, diagnosis and management of hepatitis C," *Journal of Hepatology* 32 (suppl 1):98-112.
Calisher, C. et al. (1989) "Antigenic Relationships between Flaviviruses as Determined by Cross-neutralization Tests with Polyclonal Antisera," *J.gen. Virol.* 70:37-43.
Di Bisceglie, A. et al. (1999) "Some 1.8 percent of the U.S. adult population are infected with the hepatitis C virus, most without knowing it" *Scientific American* October pp. 80-85.
Domingo, E. et al. (1985) "The quasispecies (extremely heterogeneous) nature of viral RNA genome populations: biological relevance—a review" *Gene* 40:1-8.
Dymock, B. et al. (2000) "Novel approaches to the treatment of hepatitis C virus infection," *Antiviral Chemistry & Chemotherapy* 11(2):79-96.
Fukumoto, T. et al. (1996) "Viral Dynamics of Hepatitis C Early After Orthotopic Liver Transplantation: Evidence for Rapid Turnover of Serum Virions," *Hepatology* 24:1351-1354.
Gordon, C. et al. (2005) "Control of Hepatitis C: A Medicinal Chemistry Perspective," *Journal of Medicinal Chemistry* 48(1):1-20.
Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3534.
Maradpour, D. et al. (2007) "Replication of Hepatitis C Virus," *Nature Reviews/ Microbiolory* 596:453-463.
Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.
Moennig, V. et al. (1992) "The Pestiviruses," *Advances in Virus Research* 41:53-98.

(Continued)

*Primary Examiner* — Kortney L Klinkel
*Assistant Examiner* — John Mauro
(74) *Attorney, Agent, or Firm* — Kilpatrick Townsend & Stockton LLP

(57) ABSTRACT

The present disclosure provides processes for the preparation of a compound of Formula I:

(I)

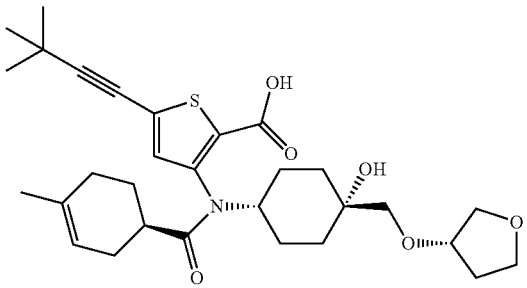

which is useful as an antiviral agent. The disclosure also provides compounds that are synthetic intermediates to compounds of formula.

32 Claims, No Drawings

(56) References Cited

OTHER PUBLICATIONS

Neumann, A. (1998) "Hepatitis C Viral Dynamics in Vivo and the Antiviral Efficacy of Interferon-α Therapy," *Science* 282:103-107.

Schul, W. (2007) "A Dengue Fever Viremia Model in Mice Shows Reduction in Viral Replication and Suppression of the Inflammatory Response after Treatment with Antiviral Drugs," *J. Infectious Disease* 195:665-674.

Scott, L. et al. (2002) "Interferon-α-2b Plus Ribavirin," *Drugs* 62:507-556.

International Search Report and Written Opinion for Application No. PCT/US2011/021279, mailed May 2, 2011.

International Search Report and Written Opinion for Application No. PCT/US2011/021335, mailed Feb. 22, 2011.

International Search Report and Written Opinion for Application No. PCT/US2010/042394, mailed Sep. 29, 2010.

International Search Report and Written Opinion for PCT/US2010/047983 mailed Nov. 15, 2010.

International Search Report and Written Opinion for PCT/US2012/046741 mailed Aug. 22, 2012.

Office Action for U.S. Appl. No. 12/838,684, mailed Aug. 2, 2012.

Notice of Allowance for U.S. Appl. No. 13/392,467, mailed Sep. 21, 2012.

Notice of Allowance for U.S. Appl. No. 13/006,761, mailed Oct. 3, 2012.

International Search Report from PCT/US2013/054405 issued Sep. 17, 2013 by the European Patent Office.

U.S. Appl. No. 13/801,011, filed Mar. 13, 2013, Watkins et al.

U.S. Appl. No. 13/800,991, filed Mar. 13, 2013, Hashah et al.

SYNTHESIS OF AN ANTIVIRAL COMPOUND

CROSS REFERENCE TO RELATED APPLICATIONS

This application claims the benefit under 35 U.S.C. §119(e) to U.S. Provisional Application Ser. No. 61/684,543, filed on Aug. 17, 2012, the entirety of which is incorporated herein by reference.

BACKGROUND

The present disclosure relates generally to the field of organic synthetic methodology for the preparation of Flaviviridae virus inhibitor compounds and their synthetic intermediates.

Viruses comprising the Flaviviridae family include at least three distinguishable genera including pestiviruses, Flaviviruses, and hepaciviruses (Calisher, et al., J. Gen. Virol., 1993, 70, 37-43). While pestiviruses, such as bovine viral diarrhea virus (BVDV), classical swine fever virus (CSFV, hog cholera) and border disease virus (BDV), cause many economically important animal diseases, their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St. Louis enchaplitis, Omsk hemorrhagic fever virus and Zika virus.

Combined, infections from the Flaviviridae virus family cause significant mortality, morbidity and economic losses throughout the world. Although compounds with anti-Flaviviridae virus activity have been disclosed, none of these are currently clinically approved antiviral therapeutics. Therefore, there remains a need to develop effective treatments for Flaviviridae virus infections. Suitable compounds for the treatment of Flaviviridae virus infections are disclosed in WO 2011/088345, including the compound of Formula I as described herein.

SUMMARY

The present disclosure provides in one embodiment a process for making a compound of Formula I:

(I)

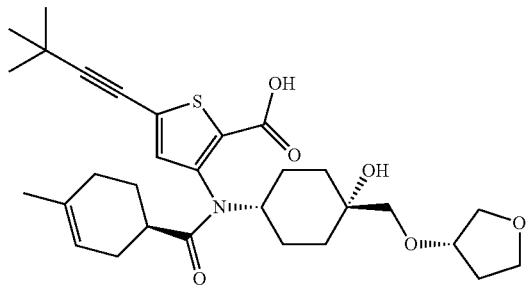

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid, or a stereoisomer, mixture of stereoisomers, pharmaceutically acceptable salt or ester thereof.

The compound of Formula I is known to be effective in the treatment of Flaviviridae virus infections (WO 2011/088345). Accordingly, a process suitable for its production of a large scale is disclosed herein. Specifically, the process disclosed herein provides the compound of Formula I without the use of protecting groups on the late stage intermediates and under mild reaction conditions such that the stereochemical integrity of the reagents and/or products is maintained.

The process disclosed herein comprises contacting a compound of Formula IV, named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof:

(IV)

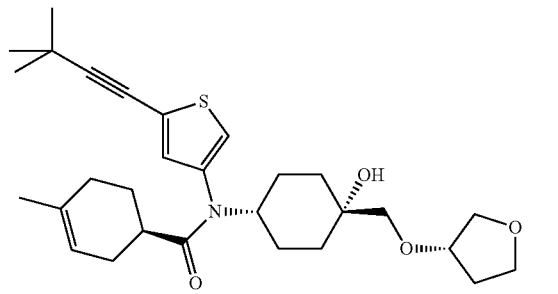

with a base in the presence of $CO_2$ under carboxylation reaction conditions to provide the compound of Formula I or a stereoisomer, mixture of stereoisomers, pharmaceutically acceptable salt or ester thereof.

In some embodiments, the present disclosure provides a process for making a compound of Formula IV:

(IV)

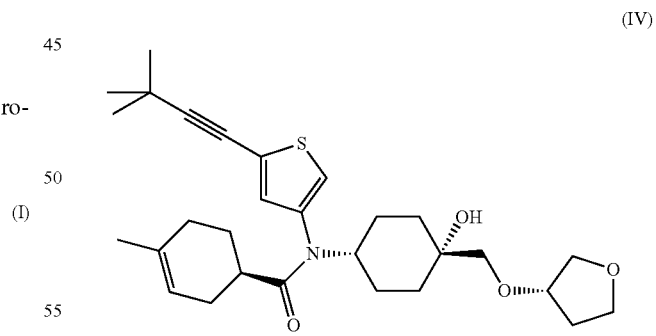

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof, comprising contacting a compound of Formula III, named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof, with a compound of Formula XI or a stereoisomer, or mixture of stereoisomers thereof:

(III)

(XI)

wherein:
X¹ is selected from the group consisting of halogen,

N, and under acylation reaction conditions to provide the compound of Formula IV or a stereoisomer, mixture of stereoisomers, or salt thereof.

In some embodiments, the present disclosure provides a process for making a compound of Formula III:

(III)

named 5-(3,3-dimethylbutyn-1-yl)-3-[(cis-4-hydroxy-4-{[(3S)-tetrahydrofuran-3-yloxy]methyl}cyclohexyl)amino] thiophene, or a stereoisomer, mixture of stereoisomers, or salt thereof, comprising contacting a compound of Formula II, named (cis-4-hydroxy-4-{[(3S)-tetrahydrofuran-3-yloxy] methyl}cyclohexyl)amine, or a stereoisomer, mixture of stereoisomers, or salt thereof, or a salt thereof with a compound of Formula X:

(II)

(X)

wherein:
$X^2$ is selected from the group consisting of halogen, triflate, and $-B(OY)_2$, wherein each Y is independently H or $C_{1-4}$ alkyl, or two Y groups together with the atoms to which they are attached form a 5- to 6-membered ring,
under N-arylation reaction conditions to provide the compound of Formula III or a stereoisomer, mixture of stereoisomers, or salt thereof.

In another embodiment, the present disclosure provides a compound of Formula III:

(III)

named 5-(3,3-dimethylbutyn-1-yl)-3-[(cis-4-hydroxy-4-{[(3S)-tetrahydrofuran-3-yloxy]methyl}cyclohexyl) amino]thiophene, or a stereoisomer, mixture of stereoisomers, or salt thereof.

In another embodiment, the present disclosure provides a compound of Formula IV:

(IV)

named 5-(3,3-dimethylbutyn-1-yl)-3-[(cis-4-hydroxy-4-{[(3S)-tetrahydrofuran-3-yloxy]methyl}cyclohexyl) {[(1R)-

4-methylcyclohex-3-en-1-yl]carbonyl}amino]thiophene, or a stereoisomer, mixture of stereoisomers, or salt thereof.

In another embodiment, the present disclosure provides a compound of Formula V:

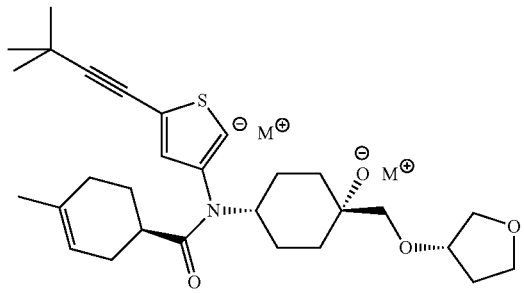

(V)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino] thiophene metal salt, or a stereoisomer or mixture of stereoisomers thereof, wherein each M is independently a metal.

In another embodiment, the present disclosure provides a compound of Formula II:

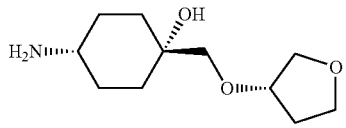

(II)

named (cis-4-hydroxy-4-{[(3S)-tetrahydrofuran-3-yloxy]methyl}cyclohexyl)amine, or a stereoisomer, mixture of stereoisomers, or salt thereof.

More specific embodiments are described below.

DETAILED DESCRIPTION

Definitions

As used in the present specification, the following words and phrases are generally intended to have the meanings as set forth below, except to the extent that the context in which they are used indicates otherwise.

The term "alkyl" as used herein refers to a straight or branched chain, saturated hydrocarbon having the indicated number of carbon atoms. For example, ($C_1$-$C_8$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein throughout.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_n R^a$, in which $R^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and $NR^a$, where $R^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_n R^a$, in which $R^a$ is alkyl, aryl or heteroaryl and n is 0, 1 or 2, or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=$CH_2$), 1-propylene (or allyl, i.e. —$CH_2$CH=$CH_2$), isopropylene (—$C(CH_3)$=$CH_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡$CCH_3$), and the like.

The term "substituted alkynyl" refers to an alkynyl group as defined above having 1 to 5 substituents (in some embodiments, 1, 2 or 3 substituents) as defined for substituted alkyl.

The term "hydroxy" or "hydroxyl" refers to a group —OH.

The term "alkoxy" refers to the group —O—R, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. The term "substituted cycloalkyl" also includes cycloalkyl groups wherein one or more of the annular carbon atoms of the cycloalkyl group has an oxo group bonded thereto. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group —O-cycloalkyl.

The term "cycloalkenyloxy" refers to the group —O-cycloalkenyl.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group —O-aryl wherein the aryl group is as defined above, and includes optionally substituted aryl groups as also defined above. The term "arylthio" refers to the group R—S—, where R is as defined for aryl.

The term "arylene" herein refers to a diradical of "aryl" as defined above that is divalent by virtue of formal removal of a hydrogen atom from the aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group —O-heteroaryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

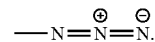

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)$_n$R$^a$, in which R$^a$ is alkyl, aryl or heteroaryl and n is 0, 1 or 2.

The term "acyl" denotes a group —C(O)R, in which R is hydrogen, optionally substituted alkyl, optionally substituted cycloalkyl, optionally substituted cycloalkenyl, optionally substituted heterocyclyl, optionally substituted aryl or optionally substituted heteroaryl.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyloxy" refers to the groups —OC(O)-alkyl, —OC(O)-cycloalkyl, —OC(O)-aryl, —OC(O)-heteroaryl and —OC(O)-heterocyclyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkoxycarbonylamino" refers to a group —N(R$^c$)C(O)OR in which R is optionally substituted alkyl and R$^c$ is hydrogen or optionally substituted alkyl.

The term "aminocarbonylamino" refers to the group —NR$^d$C(O)NRR, wherein R$^d$ is hydrogen or optionally substituted alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —$S(O)_2R$, in which R is alkyl, cycloalkyl, heterocyclyl, aryl or heteroaryl. "Substituted sulfone" refers to a group —$S(O)_2R$, in which R is substituted alkyl, substituted cycloalkyl, substituted heterocyclyl, substituted aryl or substituted heteroaryl, as defined herein.

The term "aminosulfonyl" refers to the group —$S(O)_2$NRR, wherein each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —$SO_2$-alkyl, —$SO_2$-cycloalkyl, —$SO_2$-heterocyclyl, —$SO_2$-aryl and —$SO_2$-heteroaryl.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

The term "triflate" refers to the trifluoromethanesulfonate-group (—$OSO_2$—$CF_3$).

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "alkyl-substituted phenyl", where the attachment sites are not explicit, may have any available site of the alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given Formula (e.g. the compound of Formula I) is intended to encompass the compounds of the disclosure, and the salts (e.g., pharmaceutically acceptable salts), esters, isomers, tautomers, solvates, isotopes, hydrates, co-crystals, co-formers and/or prodrugs of such compounds. Additionally, the compounds of the disclosure may possess one or more asymmetric centers, and can be produced as a racemic mixture or as individual enantiomers or diastereoisomers. The number of stereoisomers present in any given compound of a given Formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that contain stereogenic atoms which contain the same connectivity, but which differ only in the way the atoms are arranged in space. The term "stereoisomers" as used herein includes both "enantiomers" and "diastereomers".

"Enantiomers" are a pair of stereoisomers that are non-superimposable mirror images of each other and do not contain a plane of symmetry. A 1:1 mixture of a pair of enantiomers is a "racemic" mixture. The term "(±)" is used to designate a racemic mixture where appropriate.

"Diastereoisomers" are stereoisomers that have at least two stereogenic atoms and may contain a plane of symmetry, but which are not mirror-images of each other in the absence of a plane of symmetry.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−)

depending on the direction (dextro- or laevorotary) that they rotate the plane of polarized light at the wavelength of the sodium D line.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

The term "solvate" refers to a complex formed by the combining of a compound of Formula I, or any other Formula as disclosed herein, and a solvent. As used herein, the term "solvate" includes a hydrate (i.e., a solvate when the solvent is water).

The term "hydrate" refers to the complex formed by the combining of a compound of Formula I, or any Formula disclosed herein, and water.

The term "co-crystal" refers to a crystalline material formed by combining a compound of Formula I, or any Formula disclosed herein and one or more co-crystal formers (i.e., a molecule, ion or atom). In certain instances, Co-crystals may have improved properties as compared to the parent form (i.e., the free molecule, zwitter ion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

The terms "co-former" or "co-crystal former" refer to the non-ionic association of a compound of Formula I, or any Formula disclosed herein with one or more molecules, ions or atoms. Examplary co-formers can be provided with a compound and an inorganic or organic base and/or acid.

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as but not limited to $^2H$ (deuterium, D), $^3H$ (tritium) $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present disclosure, for example those into which radioactive isotopes such as $^3H$, $^{13}C$ and $^{14}C$ are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the halflife of any compound of Formula I when administered to a mammal. See, for example, Foster, "Deuterium Isotope Effects in Studies of Drug Metabolism", Trends Pharmacol. Sci. 5(12):524-527 (1984).

Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. See: P. Heinrich Stahl and Camille G. Wermuth (Eds.) Pharmaceutical Salts Properties, Selection, and Use (International Union of Pure and Applied Chemistry), Wiley-VCH; 2nd Revised Edition edition (May 16, 2011). Pharmaceutically acceptable base addition salts can be prepared from inorganic and organic bases. Pharmaceutically acceptable base addition salts may be salts prepared from inorganic and organic bases and pharmaceutically acceptable acid addition salts may be salts prepared from inorganic and organic acids.

Salts of the compounds disclosed herein can be base addition salts or acid addition salts depending on the reactivity of the functional groups present on the specific compound. Base addition salts can be derived from inorganic or organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like.

Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-NH$_2$, wherein "cycloalkenyl" is as defined herein. The term "diheteroarylamine" refers to NH(heteroaryl)$_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Acid addition salts can be derived from inorganic or organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Any of the salts disclosed herein may be optionally pharmaceutically acceptable.

The term "acylation reaction conditions" refers to the reaction conditions under which an acyl moiety is installed onto a suitable substrate, where the term "acyl" is as defined herein. "Acylation reaction conditions" typically comprise an acylating agent, such as an acyl halide, and a suitable base, such as an amine base (e.g., N,N-diisopropylethylamine, or 2,2,6,6-tetramethylpiperidine).

The term "N-arylation reaction conditions" refers to the reaction conditions under which an amine moiety is installed onto a suitable aromatic substrate, where the term "amine" is as defined herein. The "N-arylation reaction conditions" as disclosed herein typically comprise a catalyst, such as a palladium, platinum, or copper based catalyst, in the presence of a ligand, such as 5-(di-tert-butylphosphino)-1',3',5'-triphenyl-1'H-[1,4']bipyrazole, 2-(di-tert-butyl-phosphino)-1-phenyl-1H-pyrrole, 2-(di-tert-butylphosphino)-1-(2-methoxyphenyl)-1H-pyrrole, acetylacetone, acetylcyclohexanone, isobutyrylcyclohexanone, $N^1,N^2$-dimethylcyclohexane-1,2-diamine, L-proline, BINAP, or N,N-diethylsalicylamide.

The term "carboxylation reaction conditions" refers to the reaction conditions under which a carboxyl moiety is installed onto a suitable substrate, where the term "carboxyl" is as defined herein. "Carboxylation reaction conditions" typically comprise a base, which base is capable of deprotonating a carbon atom of the substrate (e.g., sodium hydride, potassium hydride, sodium hexamethyldisilazine, n-butyl lithium, n-hexyl lithium, phenyl lithium, ethyl lithium, lithium tetramethylpiperidide, or lithium diisopropylamide) and carbon dioxide.

In addition, abbreviations as used herein have respective meanings as follows:

| | |
|---|---|
| Ac | Acetate |
| Aq | Aqueous |
| BippyPhos | 5-(di-tert-butylphosphino)-1',3',5'-triphenyl-1'H-[1,4']bipyrazole |
| Bn | Benzyl |
| Boc | tert-Butoxycarbonyl |
| br. s | Broad singlet |
| Bu | Butyl |
| dba | Dibenzylideneacetone |
| DCM | Dichloromethane |
| dd | Doublet of doublets |
| ddd | Doublet of doublet of doublets |
| DMF | Dimethylformamide |
| DMSO | Dimethylsulfoxide |
| dr | Diastereomeric ratio |
| ee | Enantiomeric excess |
| Equiv/eq. | Equivalents |
| Et | Ethyl |
| ft | Foot (length) |
| g | Gram |
| GC | Gas chromatography |
| h | Hour |
| HPLC | High-pressure liquid chromatography |
| IPA | Isopropyl alcohol |
| IPAc | Isopropyl acetate |
| iPr | Isopropyl |
| kg | Kilogram |
| L | Liter |
| m | Multiplet |
| M | Molar |
| Me | Methyl |
| mg | Milligram |
| MHz | Mega hertz |
| MIBK | Methylisobutyl ketone |
| min | Minute |
| mL/ml | Milliliter |
| mmol | Millimole |
| mol | Mole |
| MTBE | Methyl-tert-butyl ether |
| N | Normal |
| NLT | No less than |
| NMR | Nuclear magnetic resonance |
| Ph | Phenyl |
| s | Singlet |
| t-Bu | tert-Butyl |
| TBS | tert-Butyldimethylsilyl |
| td | Triplet of doublets |
| Tf | Trifluoromethanesulfonate |
| THF | Tetrahydrofuran |
| TMS | Trimethylsilyl |
| TS | 4-toluenesulfonyl |
| vol | Volume |
| wt | Weight |
| δ | Chemical shift |
| μL | Microliter |

Processes

As described generally above, the disclosure provides in some embodiments processes for making a compound of Formula I.

In one embodiment, the present disclosure provides for a process for the preparation of a compound of Formula I:

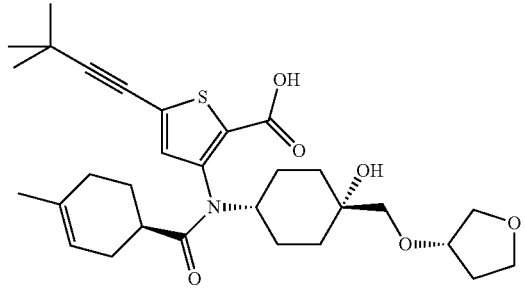
(I)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising the steps of:

a) contacting a compound of Formula II, named (cis-4-hydroxy-4-{[(3S)-tetrahydrofuran-3-yloxy]methyl}cyclohexyl)amine, or a stereoisomer, mixture of stereoisomers, or salt thereof, with a compound of Formula X:

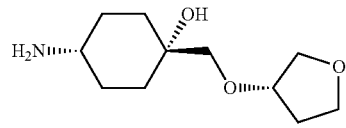
(II)

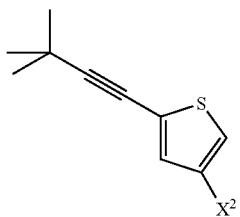
(X)

wherein:
$X^2$ is selected from the group consisting of halogen, triflate, and —$B(OY)_2$, wherein each Y is independently H or $C_{1-4}$ alkyl, or two Y groups together with the atoms to which they are attached form a 5- to 6-membered ring, under N-arylation reaction conditions to provide the compound of Formula III, named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof;

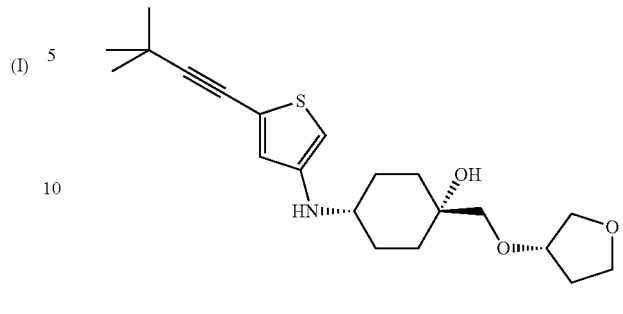
(III)

b) contacting a compound of Formula III or a stereoisomer, mixture of stereoisomers, or salt thereof, with a compound of Formula XI or a stereoisomer, or mixture of stereoisomers thereof:

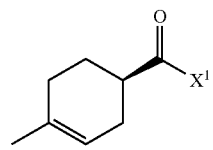
(XI)

wherein:
$X^1$ is selected from the group consisting of halogen,

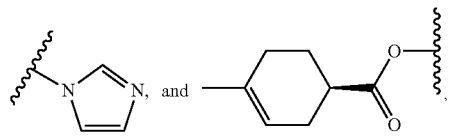 [SMILES: *n1ccnc1 ; "and" ; *OC(=O)[C@H]1CC=C(C)CC1]

under acylation reaction conditions to provide the compound of Formula IV, named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof;

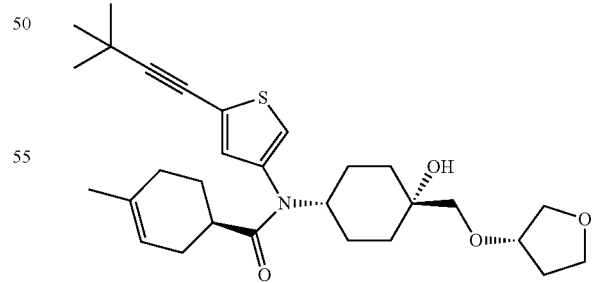
(IV)

c) contacting a compound of Formula IV or a stereoisomer, mixture of stereoisomers, or salt thereof, with a base in the presence of $CO_2$ under carboxylation reaction conditions to provide the compound of Formula I or a stereoisomer, mixture of stereoisomers, pharmaceutically acceptable salt or ester thereof.

Accordingly, one embodiment of the present disclosure provides a process for making a compound of Formula I:

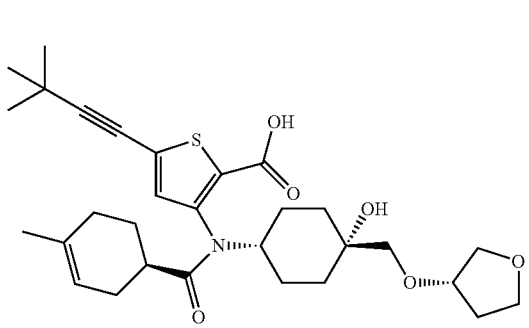
(I)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising contacting a compound of Formula IV, named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof:

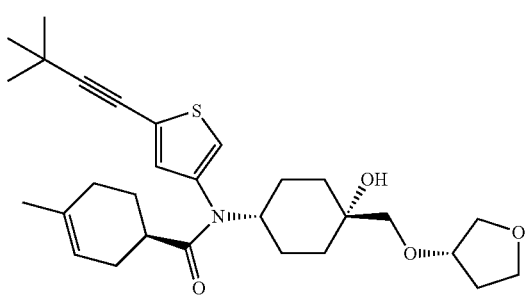
(IV)

with a base in the presence of $CO_2$ under carboxylation reaction conditions to provide the compound of Formula I or a stereoisomer, mixture of stereoisomers, pharmaceutically acceptable salt or ester thereof.

In one embodiment, the carboxylation reaction conditions of the disclosure comprise about a three-fold equivalent of the base. A variety of bases are suitable for use in the above reaction, provided the base is capable of deprotonating the thiophene. Non-limiting examples of suitable bases include sodium hydride, potassium hydride, sodium hexamethyldisilazine, n-butyl lithium, n-hexyl lithium, phenyl lithium, ethyl lithium, lithium tetramethylpiperidide, and lithium diisopropylamide. In certain embodiments, a first base may be used to deprotonate only the hydroxyl group of Formula IV, followed by use of a stronger base capable of deprotonating the thiophene. For example, one embodiment includes first treating a compound of Formula IV with a Grignard reagent (e.g., an alkyl- or aryl-magnesium halide), followed by a base as disclosed above (e.g., a lithium base).

In certain embodiments, the carboxylation temperature is from about −78° C. to about 45° C. In other embodiments, the carboxylation reaction temperature is from about −20° C. to about 20° C.

In some embodiments, the present disclosure provides a process for making a compound of Formula IV:

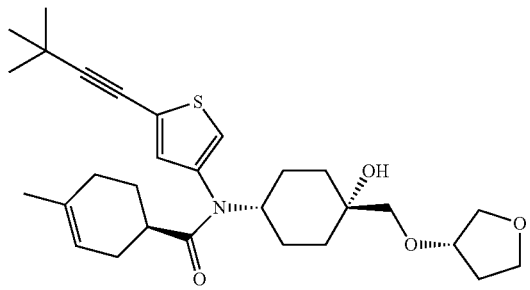
(IV)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof, which process comprises contacting a compound of Formula III, named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof, with a compound of Formula XI or a stereoisomer, or mixture of stereoisomers thereof:

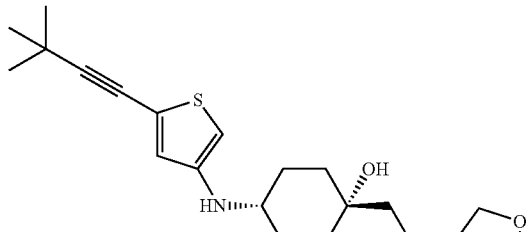
(III)

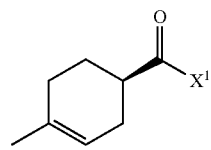
(XI)

wherein:
$X^1$ is selected from the group consisting of halogen,

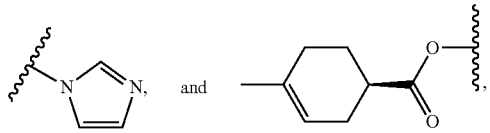 [SMILES: *n1ccnc1 ; "and" ; *OC(=O)[C@H]1CC=C(C)CC1 ; ","]
and under acylation reaction conditions to provide the compound of Formula IV or a stereoisomer, mixture of stereoisomers, or salt thereof.

In one embodiment, the acylation reaction conditions comprise a base. Suitable bases include substituted or unsubstituted tertiary amines, which includes amines where the three substituents, together with the amino nitrogen, form a heteroaryl group. In a further embodiment, the base is imidazole, pyridine, N,N-diisopropylethylamine or 2,2,6,6-tetramethylpiperidine.

In another embodiment, the acylation reaction conditions of the disclosure comprise a temperature from about −45° C. to about 100° C., or from about −45° C. to about 45° C., or in one embodiment, the acylation reaction conditions comprise a temperature from about 0° C. to about 20° C.

A variety of acylating agents (e.g., carbodiimides, N-methylimidazoles, and the like) and/or other derivatives of Formula XI (e.g., activated esters, mixed anhydrides, acyltriazines, activated phosphates, organophosphorous esters, and the like) are suitable for use in the acylation reaction. In certain embodiments of the methods disclosed above, $X^1$ is halogen. In some embodiments, $X^1$ is chloro.

In some embodiments, the present disclosure provides a process for making a compound of Formula III:

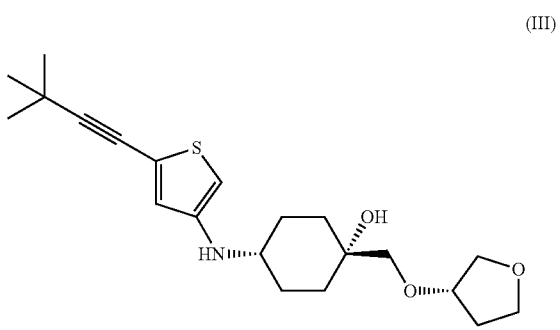 [SMILES: CC(C)(C)C#Cc1cc(N[C@H]2CC[C@](O)(CO[C@H]3CCOC3)CC2)cs1]

(III)

named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof, comprising contacting a compound of Formula II, named (cis-4-hydroxy-4-{[(3S)-tetrahydrofuran-3-yloxy]methyl}cyclohexyl)amine, or a stereoisomer, mixture of stereoisomers, or salt thereof, with a compound of Formula X:

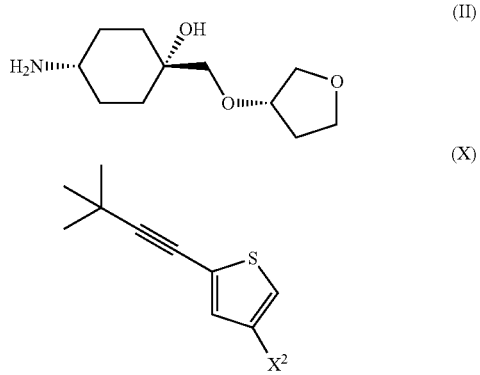

(II)

(X)

wherein:

$X^2$ is selected from the group consisting of halogen, triflate, and —B(OY)$_2$, wherein each Y is independently H or $C_{1-4}$ alkyl, or two Y groups together with the atoms to which they are attached form a 5- to 6-membered ring, under N-arylation reaction conditions to provide the compound of Formula III or a stereoisomer, mixture of stereoisomers, or salt thereof.

A variety of other N-arylating agents are also suitable for use in the N-arylation reaction. Non-limiting examples include cyclic organoboron compounds such as boroxines, boronates, and the like. In certain embodiments of the methods disclosed above, $X^2$ is halogen. In some embodiments, $X^2$ is bromo.

In one embodiment, the N-arylation reaction conditions of the disclosure comprise a catalyst. In a further embodiment, the catalyst is a palladium, platinum, or copper based catalyst. In another embodiment, the catalyst is selected from the group consisting of copper(I) chloride, tris(dibenzylideneacetone)dipalladium(0), copper(II) chloride, copper(I) bromide, copper(II) bromide, copper(I) acetate, copper(II) acetate, copper(II) acetylacetonate, copper(I) trifluoromethanesulfonate, copper(II) trifluoromethanesulfonate, copper(I) thiophene-2-carboxylate, and copper(I) iodide.

In another embodiment, the N-arylation reaction conditions of the disclosure further comprise a ligand. In a further embodiment, the ligand is selected from the group consisting of 5-(di-tert-butylphosphino)-1',3',5'-triphenyl-1'H-[1,4]bipyrazole, 2-(di-tert-butyl-phosphino)-1-phenyl-1H-pyrrole, 2-(di-tert-butylphosphino)-1-(2-methoxyphenyl)-1H-pyrrole, acetylacetone, acetylcyclohexanone, isobutyrylcyclohexanone, $N^1,N^2$-dimethylcyclohexane-1,2-diamine, L-proline, BINAP, and N,N-diethylsalicylamide.

In another embodiment, the N-arylation reaction conditions of the disclosure further comprise a base. Exemplary bases include metal hydroxides, carbonates, alkoxides, and the like. In certain embodiments, the base is selected from the group consisting of potassium hydroxide, sodium hydroxide, sodium tert-amylate, cesium carbonate, cesium hydroxide, potassium phosphate tribasic, sodium tertbutoxide, sodium methoxide, and sodium ethoxide.

In certain embodiments, the N-arylation reaction conditions of the disclosure further comprise a phase transfer catalyst. For example, in some embodiments, the phase transfer catalyst is cetyltrimethyl ammonium bromide.

In the methods disclosed above, the compound of Formula II can be any form which includes the compound of Formula II, such as the free base or salt thereof. Accordingly, in some embodiments, the compound of Formula II is the free base. In another embodiment, the compound of Formula II is a salt. Non-limiting examples of salts of Formula II include such salts as the hydrochloric acid salt or the (S)-mandelic acid salt. Thus, in some embodiments, the compound of Formula II is the (S)-mandelic acid salt thereof.

The intermediates in the process for the synthesis of Formula I can be used in the next step with or without purification. The conventional means of purification include recrystallization, chromatography (e.g., adsorbant, ion exchange and HPLC), and the like.

In some embodiments, the means of purification can include chiral resolution in order to increase the enantiomeric purity of one or more intermediates in the process for the synthesis of Formula I and/or Formula I. Such methods can include for example, crystallization, a chiral resolving agent, and/or chiral chromatography. For example, in some embodiments, compounds of Formula I can be further purified via crystallization with cinchonine alkaloids.

Compounds

In other embodiments, the disclosure provides for intermediate compounds that are useful in the processes described herein. Thus, for instance, one embodiment is a compound of Formula III:

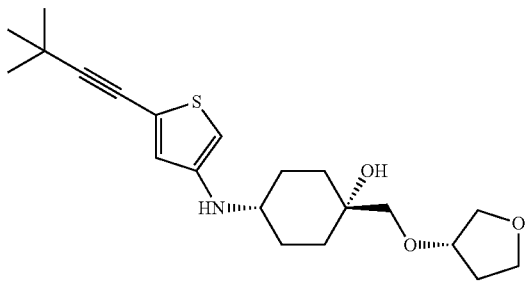

(III)

named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof.

In another embodiment, the disclosure provides a compound of Formula IV:

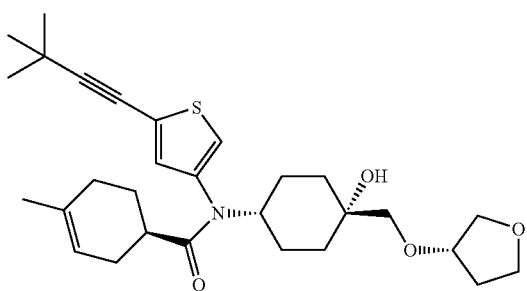

(IV)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof.

In another embodiment, the disclosure provides a compound of Formula V:

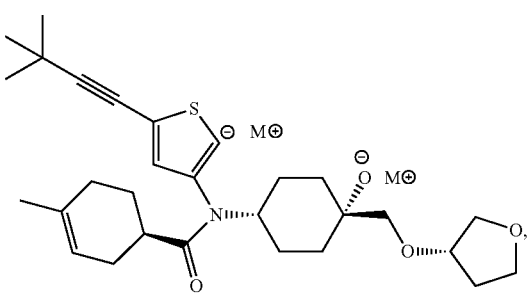

(V)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene metal salt, or a stereoisomer, mixture of stereoisomers thereof, wherein each M is independently a metal. In some embodiments, the metal is lithium, potassium, or sodium. In certain embodiments, the metal is lithium. In certain embodiments, each M represents the same metal. In other embodiments, as different bases and/or organomettalic reagents can be used to deprotonate the hydroxyl group and the thiophene in Formula IV in order to provide Formula V, each M can represent a different metal. In such instances, examples of suitable metals include lithium, potassium, sodium, magnesium halides, zinc halides, etc.

In another embodiment, the disclosure provides a compound of Formula II:

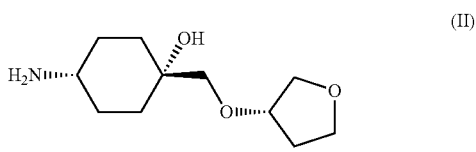 [SMILES: N[C@H]1CC[C@](O)(CO[C@H]2CCOC2)CC1]

(II)

named (cis-4-hydroxy-4-{[(3S)-tetrahydrofuran-3-yloxy]methyl}cyclohexyl)amine, or a stereoisomer, mixture of stereoisomers, or salt thereof. In some embodiments, the compound of Formula II is the free base. However, in other embodiments, the compound of Formula II is a salt. Various salts are contemplated herein, including but not limitied to the hydrochloric acid salt or the (S)-mandelic acid salt of Formula II. In certain embodiments, the compound of Formula II is the (S)-mandelic acid salt thereof, represented by Formula IIA:

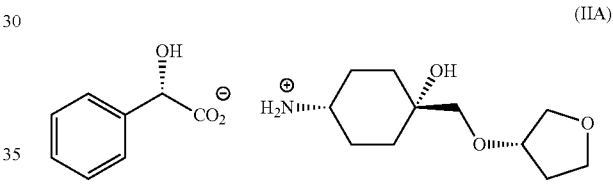

(IIA)

named (cis-4-hydroxy-4-{[(3S)-tetrahydrofuran-3-yloxy]methyl}cyclohexyl)ammonium (S)-mandelate salt, or a stereoisomer, mixture of stereoisomers, or salt thereof.

Co-formers and/or co-crystals of any one of the Formulas disclosed herein are also provided. For example, in some embodiments, the compound of Formula II may form a co-crystal, such as (cis-4-hydroxy-4-{[(3S)-tetrahydrofuran-3-yloxy]methyl}cyclohexyl)amine (S)-mandelic acid co-crystal.

The present disclosure is not to be limited in scope by the specific embodiments disclosed in the examples, which are intended to be illustrations of a few embodiments of the disclosure, nor is the disclosure to be limited by any embodiments that are functionally equivalent within the scope of this disclosure. Indeed, various modifications of the disclosure in addition to those shown and described herein will become apparent to those skilled in the art and are intended to fall within the scope of the appended claims. To this end, it should be noted that one or more hydrogen atoms or methyl groups can be omitted from the drawn structures consistent with accepted shorthand notation of such organic compounds, and that one skilled in the art of organic chemistry would readily appreciate their presence.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Example 1

Preparation of 5-(3,3-Dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (I)

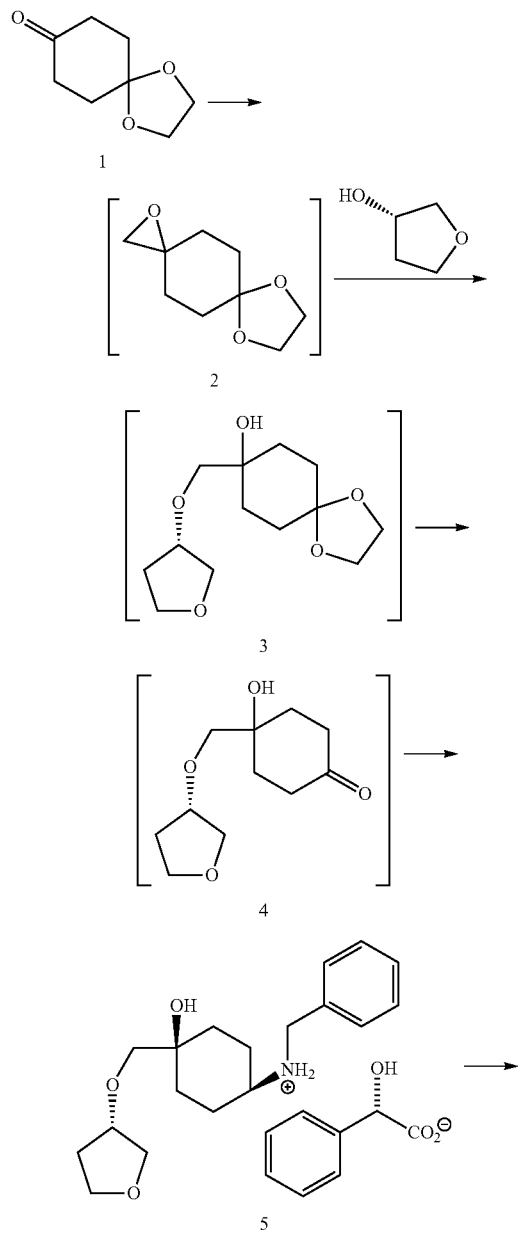

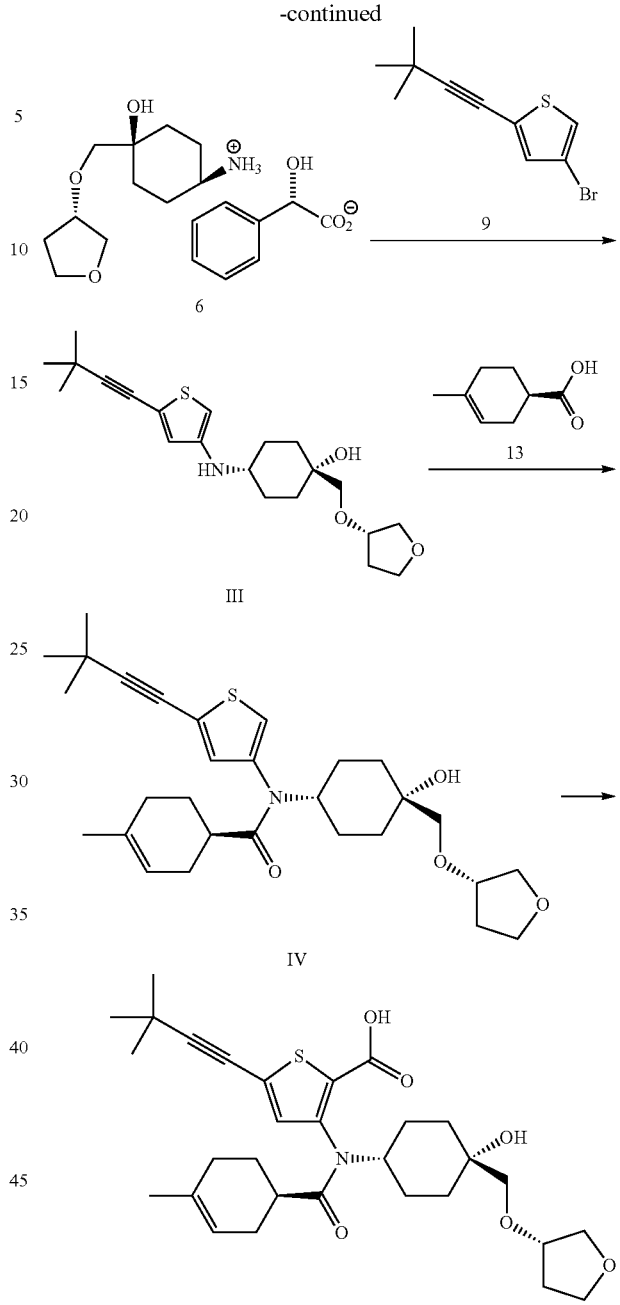

I. Synthesis of Starting Materials

A. Epoxidation, Etherification, Deketalization, Reductive Amination, and Deprotection to Provide Intermediate 6:

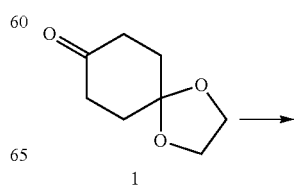

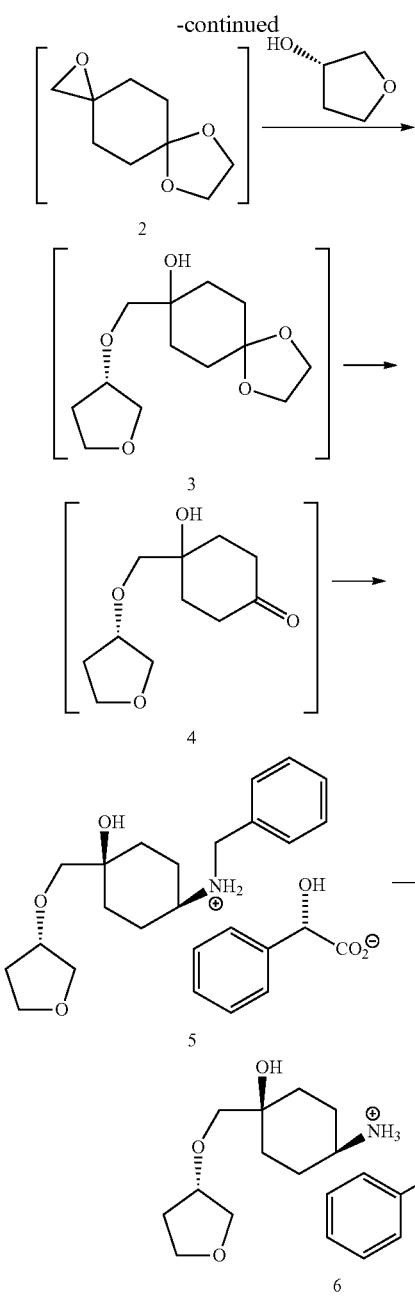

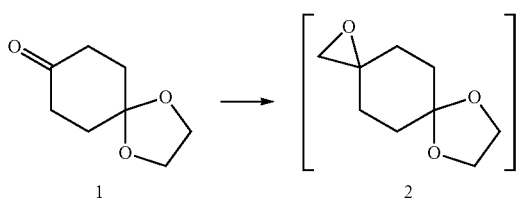

i. Epoxidation to Prepare Intermediate 2:

The epoxidation of 1 to provide 2 was performed using the following procedure. Charge lithium tert-butoxide (1.14 kg, 1.1 equiv) and trimethylsulfoxonium iodide (3.12 kg, 1.1 equiv) to an inerted 70 L reactor with the jacket temperature set to 23° C. Charge DMSO (13.8 kg) and vigorously mix contents between 20 and 25° C. for one hour. Charge 1,4-cyclohexanedione monoethylene acetal (1) (2.02 kg, 1.0 equiv) to the reactor. Once reaction is complete, charge the reactor with brine (18 L, 15 wt %) at a rate to ensure the reaction temperature does not exceed 40° C. Extract the homogenous brine containing reaction mixture with MTBE (3×30 kg) and combine the product containing organics. Concentrate the combined organics by distillation at ambient pressure. Distill off the MTBE to 5 volumes (10 L) to provide a solution of 2 in MTBE.

$^1$H NMR (400 MHz, CDCl$_3$) δ 4.02-3.91 (m, 4H), 2.67 (s, 2H), 1.95-1.83 (m, 4H), 1.81-1.72 (m, 2H), 1.60-1.53 (m, 2H).

However, alternatives to the epoxidation reagents and/or reaction conditions just described are also encompassed in the present disclosure.

For example, the epoxidation reagent can be trimethylsulfoxonium chloride, trimethylsulfonium iodide, or trimethylsulfonium chloride; the base can be potassium tert-amylate, lithium tert-butoxide, sodium tert-butoxide, sodium hydride, potassium hydride, or potassium hydroxide; the solvent can be methyl tert-butyl ether, 2-methyltetrahydrofuran, dichloromethane, or DMF; and/or the temperature can be between about 0 to about 40° C.

It is also possible, in accordance with other embodiments, to epoxidize 1 under other epoxidation reagents, such as dibromomethane with n-butyllithium in tetrahydrofuran.

ii. Etherification to Prepare Intermediate 3:

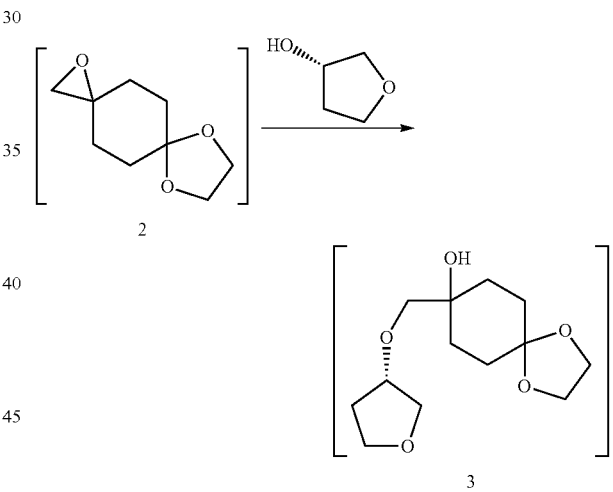

The etherification of 2 to provide 3 was performed using the following procedure. Charge the solution of 2 in MTBE, (S)-tetrahydrofuran-3-ol (1.25 kg, 1.1 equiv), and potassium tert-butoxide (1.59 kg, 1.1 equiv) to an inerted 70 L reactor and heat contents to 55 to 60° C. Upon reaction completion, cool the reactor contents to ambient to afford a solution of 3 in MTBE.

$^1$H NMR (400 MHz, CDCl$_3$) δ 4.19-4.09 (m, 1H), 4.00-3.66 (m, 8H), 3.27 (dd, J=20.1, 8.8 Hz, 2H), 2.04-1.84 (m, 6H), 1.76-1.68 (m, 2H), 1.67-1.50 (m, 2H).

However, alternatives to the etherification reagents and/or reaction conditions just described are also encompassed in the present disclosure.

In other embodiments, alternative bases are suitable in the above reaction, such as potassium tert-amylate, lithium tert-butoxide, sodium tert-butoxide, sodium hydride, potassium hydride, potassium hydroxide, potassium and sodium metal, or cesium carbonate. Other solvents are also suitable, such as tetrahydrofuran, dimethylsulfoxide, dichloromethane, toluene, 2-methyltetrahydrofuran. Acceptable temperatures can range from about 10 to about 70° C.

iii. Deketalization to Prepare Intermediate 4:

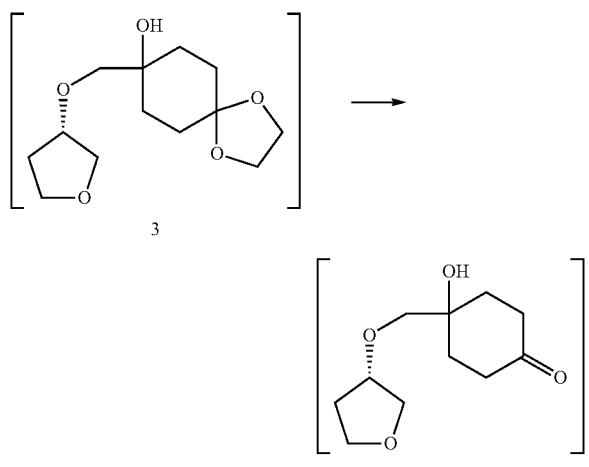

The deprotection of 3 to provide 4 was accomplished according to the following procedure. Charge HCl (13.3 L, 1.5 N) to the reactor containing a solution of 3 in MTBE (2.4 kg, 11.1 mmol). Mix the biphasic reaction mixture between 18 and 25° C. Once the reaction is complete, stop agitation and separate the two phases. Extract the aqueous phase with $CH_2Cl_2$ (2×20 L). Combine organic phases in the reactor. Charge aqueous $NaHCO_3$ (15 L, 7.5 wt %) and mix for 1 hour, let settle and split phases. Return organic phase to reactor. Concentrate organics to 5 vol (10 L). Charge 12 L of ethanol and concentrate to 8.5 L to afford 4 as a solution in EtOH.

$^1$H NMR (400 MHz, $CDCl_3$) δ 4.17 (m, 1H), 3.95-3.75 (m, 4H), 3.35 (AB, 2H), 2.74 (td, J=13.6, 6.7 Hz, 2H), 2.10-1.97 (m, 5H), 1.71 (td, J=13.6, 6.7 Hz, 2H).

However, alternatives to the reagents and/or reaction conditions just described are also encompassed in the present disclosure. For example, in addition to hydrochloric acid, the deketalization catalyst can be sulfuric acid, trifluoroacetic acid, hydrobromic acid, triflic acid, p-toluenesulfonic acid, benzene sulfonic acid, methane sulfonic acid, pyridinium tosylate, or acetic acid. Additional solvents and solvent combinations can also be employed. These include tetrahydrofuran, acetone, acetic acid, and dioxane. Acceptable temperatures can range from about 10 to about 45° C.

iv. Reductive Amination to Prepare Intermediate 5:

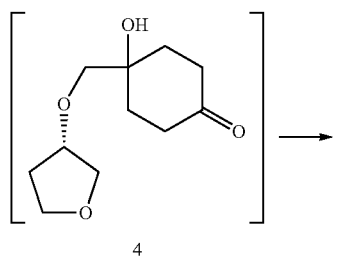

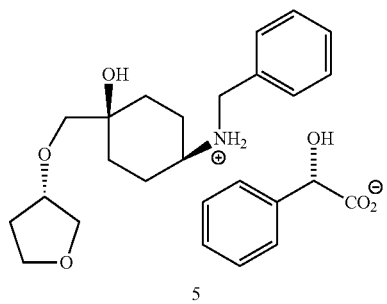

Intermediate 5 was prepared from 4 using benzylamine under the following reductive amination reagents and reaction conditions. Charge the EtOH solution of 4 to the 70 L reactor (7.84 kg, 30.3 wt %, by $^1$H-NMR), and set the jacket temperature to 20° C. Charge $Ti(OiPr)_4$ (4.0 kg, 1.25 equiv) at a pace to keep the reaction temperature below 30° C. Charge benzylamine (1.2 kg, 1.0 equiv) at a rate to keep the reaction temperature below 35° C. Agitate the reaction mixture for 1 hour at 20° C., then cool the reaction mixture to −4° C. Dissolve sodium borohydride (210 g, 0.5 equiv) in EtOH (5.8 L), and charge to the reaction mixture at a rate to maintain a reaction temperature of not more than 0° C. After 1 hour, add 20 wt % trisodium citrate solution (38 L) and 4-methylpentan-2-one (MIBK, 19.2 L) and set the jacket temperature to 20° C. Agitate the mixture vigorously for 30 minutes, and settle layers. Discard the aqueous layer, and wash the organic phase with 15 wt % NaCl (19 L). Concentrate the organic phase under reduced pressure to an oil. Charge MIBK (7.1 L, 3 vol) and polish filter the turbid solution through a 0.6 micron filter. Transfer the filtrate to the 70 L reactor and charge (S)-mandelic acid (1.7 kg, 1.0 equiv) followed by a small amount of seed crystal. Age the slurry for at least 1 hour, and then add MTBE (9.6 L, 4 vol) over 15 minutes. Filter the slurry and wash the cake with 8.7 L 2/1 MIBK/MTBE. Dry the solid in vacuum oven to afford 5 as white solid.

$^1$H NMR (400 MHz, $CD_3OD$) δ 7.60-7.38 (m, 7H), 7.32-7.18 (m, 3H), 4.21-4.09 (m, 3H), 3.89-3.71 (m, 4H), 3.34-3.19 (m, 2H), 3.12-2.97 (m, 1H), 2.34 (d, J=7.1 Hz, 1H), 1.96 (ddd, J=46.9, 24.1, 3.7 Hz, 2H), 1.85-1.65 (m, 4H), 1.51 (td, J=13.7, 3.7 Hz, 2H).

However, alternative reductive amination reagents and/or reaction conditions to those just described are also encompassed in the present disclosure.

For instance, alternative reductive amination reagents can be used, which includes but is not limited to, titanium tetraethoxide. In addition to sodium borohydride, other reductants may also be employed, such as sodium cyanoborohydride, sodium triacetoxyborohydride, lithium borohydride, potassium borohydride, sodium bis(2-methoxyethoxy)aluminumhydride, lithium tri-tert-butoxyaluminum hydride, sodium tri-methoxyborohydride, and sodium tri-(2-ethylhexanoyloxy)borohydride.

Other solvents and solvent combinations are suitable for the reductive amination. For instance, these include isopropanol, methanol, dichloromethane, dichloroethane, tetrahydrofuran, methyl tert-butyl ether, acetonitrile, toluene, and dimethyl acetamide.

Acceptable temperatures can range from about −15 to about 25° C., although are typically from −4 to about 5° C.

v. Hydrogenolysis to Prepare Intermediate 6:

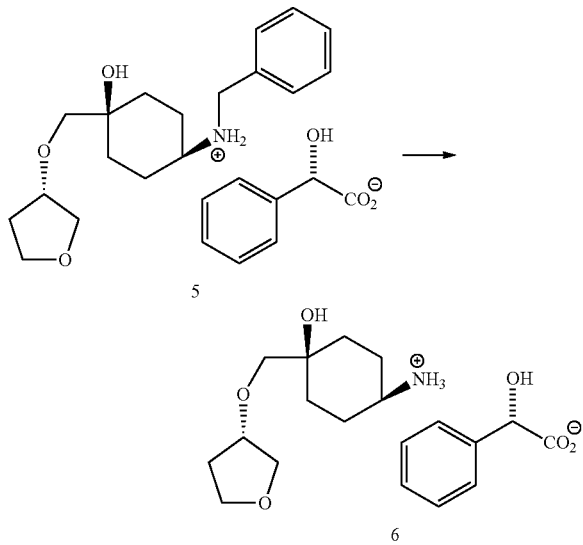

The deprotection of 5 to provide 6 was performed using the following procedure. Charge 5 (2.20 kg, 1 equiv) and Pd(OH)$_2$/C (0.12 kg, 20 wt % dry basis, 0.02 equiv) to a 70 L reactor. Inert the reactor and charge MeOH (25.8 L, 10 vol) and ammonium formate (1.52 kg, 5.0 equiv). Warm the reactor contents to 48-50° C. under positive nitrogen pressure and agitate. When the reaction is complete, cool the reaction mixture to 18 to 25° C., and filter the reaction mixture to remove the solids. Solvent exchange through distillation under reduced pressure to isopropanol (IPA) targeting a final volume of 12 L (5 vol). Filter the slurry and wash the cake with IPA (4 L, 2 vol). Dry the solid in vacuum oven at 40° C. to obtain 6 as white solid.

$^1$H NMR (400 MHz, CD$_3$OD) δ 7.50-7.42 (m, 2H), 7.33-7.15 (m, 3H), 4.15-4.06 (m, 1H), 3.92-3.59 (m, 4H), 3.37-3.13 (m, 4H), 2.94 (td, J=10.7, 5.6 Hz, 1H), 1.97 (td, J=7.7, 4.4 Hz, 2H), 1.87-1.59 (m, 7H), 1.55-1.39 (m, 2H).

However, alternative deprotection conditions to those just described are also encompassed in the present disclosure. For example, any suitable palladium catalyst can be used (e.g., palladium hydroxide on carbon or palladium on carbon); any suitable hydrogen source can be used (e.g., ammonium formate, formic acid, hydrogen gas, triethylammonium formate, cyclohexene, etc.); temperatures can range from about 20 to about 50° C.; and the solvent can be any suitable solvent (e.g., methanol, ethanol, tetrahydrofuran, etc.).

B. Synthesis of Intermediate 9:

1. Bromination, De-Bromination, and Alkynylation to Provide Intermediate 9:

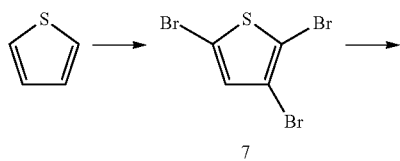

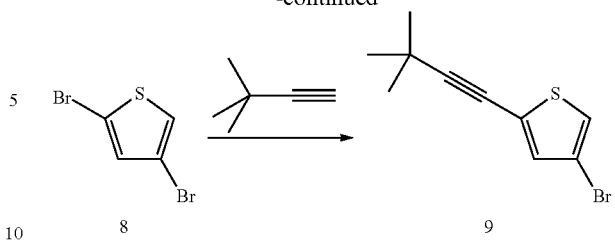

i. Bromination to Prepare Intermediate 7:

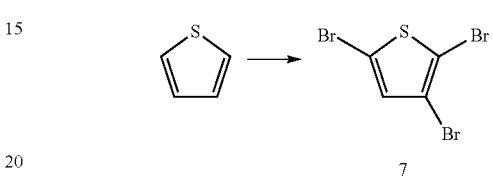

Thiophene was brominated to provide 7 according to the following procedure. A reactor was charged with a solution of aqueous hydrobromic acid (47.6%, 125.0 kg, 5 equiv). Thiophene (12.5 kg, purity 99%, 1 equiv) was added to it at 25-30° C. Tetrabutylammonium bromide (0.625 kg, 0.13 equiv) was added to the reaction mass. The reaction mass was heated to 50-55° C. 50% Aqueous hydrogen peroxide solution (31.3 kg, 3.1 equiv) was added to the reaction mass over 10 h keeping the temperature in the range of 50-55° C. The reaction mass was then heated to 70-75° C. After reaction completion, the reaction mass was cooled to 20-25° C. and washed with 20% sodium metabisulphite solution (17 L), 2 N sodium hydroxide solution (62 L) and the crude product was subjected to fractional distillation to afford 2,3,5-tribromothiophene. The spectral properties of this molecule are consistent with commercially available material.

However, alternative reagents and/or reaction conditions to those disclosed above may also be employed in the bromination reaction. For example, bromination reagents such as bromine, sodium bromate and sulfuric acid, or N-bromosuccinimide may be used. Alternative solvents include carbon tetrachloride, chloroform, acetic acid, dichloromethane, or DMF; and acceptable temperatures range from about −78 to 75° C.

ii. De-Bromination to Prepare Intermediate 8:

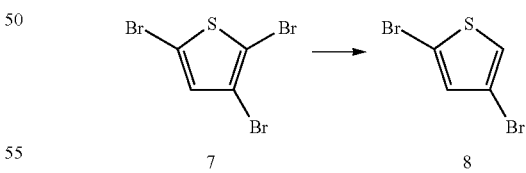

Selective de-bromination of 7 provided 8 according to the following procedure. Dimethyl sulfoxide (DMSO, 330 L) was charged to reactor. 2,3,5-tribromothiophene (33 kg, 1.0 equiv) was charged to the reaction mass under stirring. The reaction mass was cooled to 15-20° C. Sodium borohydride (7.8 kg, 2.0 equiv) was charged lot wise to the reaction mass in 2.0 h maintaining temperature 15 to 20° C. The reaction mass was heated to 20 to 25° C. and maintained until the reaction was completed. The reaction mass was quenched in water (660 L) at 10 to 15° C. and the product was extracted into toluene (5×165 L). The combined organic layer was washed with water (165 L). The organic layer was dried over anhydrous sodium sulfate (8.0 kg) and concentrated under reduced pressure below 50° C. to yield 2,4 dibromothiophene. The spectral properties of this molecule are consistent with commercially available material.

However, alternative reagents and/or reaction conditions to those disclosed above may also be employed in the de-bromination reaction. For example, reductants such as lithium borohydride, potassium borohydride, butyl lithium, zinc, magnesium, or lead (II) acetate can be utilized. Other solvents suitable for the de-bromination reaction include tetrahydrofuran, diethylether, acetic acid, water, or dichloromethane. Acceptable temperatures can range from about −78 to about 77° C.

iii. Alkynylation to Provide Intermediate 9:

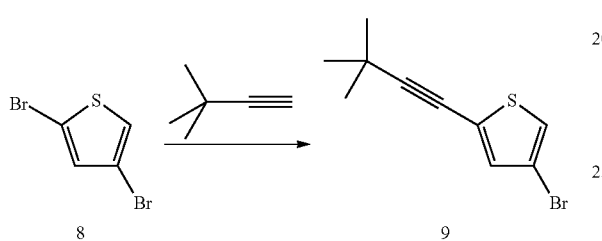

The alkynylation of 8 to provide 9 was performed using the following procedure. A reactor was evacuated and flushed with nitrogen (extra pure). Dimethyl formamide (560 L) and 2,4-dibromothiophene (37.5 kg, 1.0 equiv) were charged to the reactor. The reaction mass was cooled to 20-25° C. Palladium chloride bis triphenyl phosphine complex (3 kg, 0.03 equiv) was charged to the reaction mass followed cuprous iodide (1.6 kg, 0.06 equiv), t-butyl acetylene (13.0 kg, 1.1 equiv) and triethylamine (43 kg, 3.0 equiv). The reactor was again flushed with nitrogen and pressurized with 0.50 kg nitrogen (extra pure) pressure. The reaction mass was heated to 25-30° C. and agitated until reaction completion (ca. 6 h). The reaction mass was filtered and the filter cake was washed with dimethyl formamide (37.5 L). The filtrate was concentrated under reduced pressure at a temperature below 50° C. The residue was dissolved in heptane (187.5 L) at 25 to 30° C. The solids were filtered off and washed with heptane (3×56 L). The filtrate was washed successively with 5% ammonia solution and saturated NaCl solution. The organic layer was further dried over anhydrous sodium sulfate and concentrated under vacuum at a temperature below 70° C. The crude oil was purified by fractional distillation to provide 9.

$^1$H NMR (400 MHz, CDCl$_3$) δ 7.00 (s, 1H), 6.96 (s, 1H), 1.26 (s, 9H).

However, alternative reagents and reaction conditions to those disclosed above may also be employed in the alkynylation reaction. For example, reagents such as morpholine, diisopropylamine, piperidine, or pyrollidine, catalysts such as palladium (II) acetate and triphenylphosphine, or tetrakis(triphenylphosphine)palladium, solvents such as benzene, tetrahydrofuran, N-methylpyrrolidinone, or pyrollidine, and temperatures ranging from about 20 to about 70° C. may be employed.

2. Acylation/Bromination, De-Bromination, Vinyl Chloride Formation, Dehydrochlorination to Provide Intermediate 9:

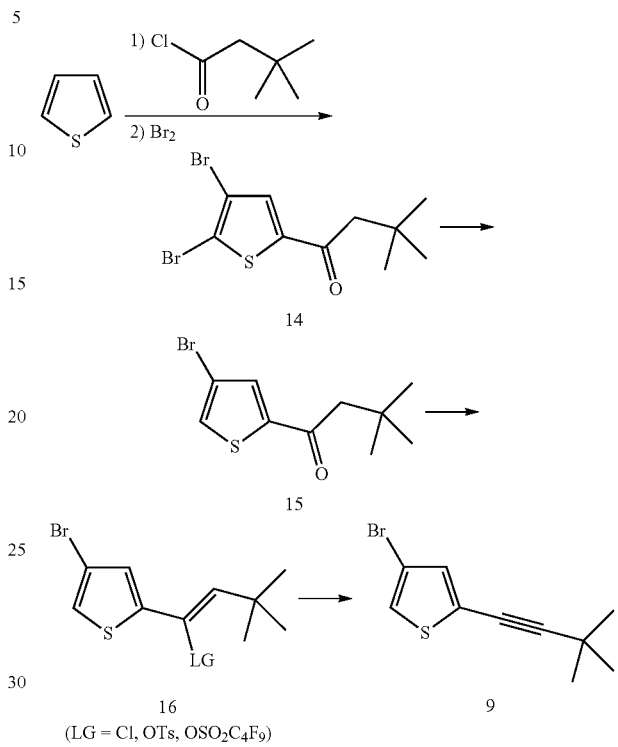

i. Acylation/Bromination to Prepare Intermediate 14

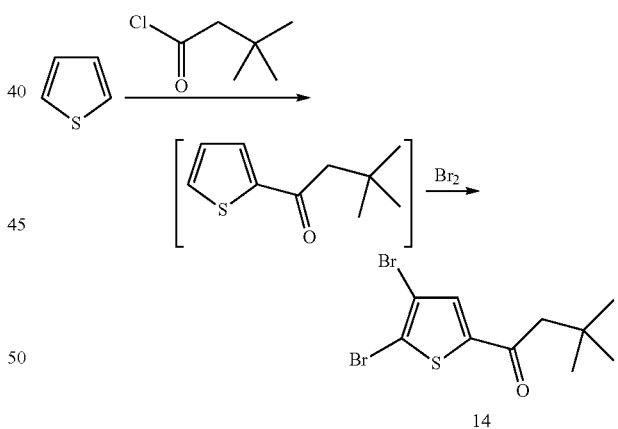

Thiophene was acylated and brominated to provide 14 according to the following procedure. A reaction vessel was charged with AlCl$_3$ (36.7 g, 275 mmol, 2.2 eq.) and dichloromethane (DCM) (50 ml, 5 ml/g). The resulting contents were cooled to −5° C. to 0° C. and a solution of 3,3-dimethylbutyryl chloride (19.1 ml, 138 mmol, 1.1 eq.) in DCM (50 ml, 5 ml/g) was added while maintaining content temperature below 10° C. After stirring for 15 minutes, a solution of thiophene (10 ml, 125 mmol, 1.0 eq.) in DCM (50 ml, 5 ml/g) was added while maintaining content temperature below 10° C. The resulting red mixture was stirred until reaction completion as monitored by HPLC. Bromine (14 ml, 275 mmol, 2.2 eq.) was then added slowly over 2 hours. The reaction mixture was stirred at ambient temperature until completion as monitored by HPLC. The reaction mixture was transferred to a vessel containing ice water (200 ml; 20 ml/g), rinsed with DCM (25 ml, 2.5 ml/g) and water (25 ml, 2.5 ml/g), stirred for 1 hour and the layers separated. The organic layer was washed with 1M aq. NaOH (100 ml, 10 ml/g) and 15% aq. NaCl (100 ml, 10 ml/g) and dried over MgSO$_4$. After filtration to remove the drying agent, the organic layer was concentrated under vacuum to ~100 ml (~10 ml/g) volume, co-evaporated under vacuum with isopropyl alcohol (IPA) (100 ml) and the final volume adjusted to ~100 ml (~10 ml/g). A seed crystal of dibromide 4 (10 mg, 1 mg/g) was then added. After stirring for 1 hour, water (25 ml, 2.5 ml/g) was added over 15 minutes and the mixture was stirred for 1 hour at ambient temperature followed by 1 hour at 0° C. to 5° C. The solids were collected via filtration, rinsed with the filtrate and with 50% aq. IPA (20 ml, 2 ml/g), and dried at 35° C. in a vacuum oven to afford dibromide 14 (35.4 g, 83% yield) as a pale yellow solid.

$^1$H NMR (400 MHz, CDCl$_3$) δ 7.45 (s, 1H), 2.67 (s, 2H), 1.05 (S, 9H).

However, alternative reagents and reaction conditions to those disclosed above may also be employed. In the acylation reaction for example, reagents such as N-butyl-N-methylimidazolium hexafluorophosphate, 3,3-dimethylbutanoic anhydride, indium(III) chloride, 3,3-dimethylbutanoic acid, trifluoromethanesulfonic anhydride, phosphoric acid, tin(II) triflate, ytterbium(III) triflate, zinc triflate, trifluoroacetic acid, butyllithium, tin(IV) chloride, phosphorous pentoxide, tin(II) chloride, zinc(II) chloride, borontrifluoride etherate, lithium diisopropylamide, or titanium(IV) chloride, solvents such as carbon tetrachloride, tetrachloroethylene, nitromethane, trifluoroacetic acid, nitrobenzene, diethyl ether, benzene, pentane, or tetrahydrofuran, and temperatures ranging from about −20 to about 115° C. may be employed. In the bromination reaction for example, reagents such as hydrobromic acid, sodium bromide, sodium bromate, sulfuric acid, N-bromosuccinimide, aluminum trichloride, potassium acetate, benzyltrimethylammonium bromate, zinc chloride, or 1,3-dibromo-5,5-dimethylhydantoin, solvents such as water, diethyl ether, chloroform, ethanol, dichloroethane, acetic acid, dimethylformamide, tetrahydrofuran, trifluoroacetic acid, carbon tetrachloride, or cyclohexane, and temperatures ranging from about 0 to about 100° C. may be employed.

ii. De-Bromination to Prepare Intermediate 14

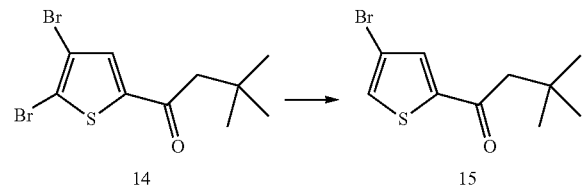

Intermediate 14 was de-brominated to provide 15 according to the following procedure. A reaction vessel was charged with dibromide 14 (35.0 g, 103 mmol), zinc dust (7.07 g, 108 mmol, 1.05 eq.) and water (210 ml, 6 ml/g). To the resulting suspension was added AcOH (52.5 ml, 1.5 ml/g). The reaction mixture was stirred at 80° C. until reaction completion as monitored by HPLC. The reaction mixture was cooled to ambient temperature and hexanes (175 ml, 5 ml/g) was added. After stirring for 15 minutes, the layers were separated and the organic layer was washed with 1N aq. NaOH (175 ml, 5 ml/g) and 15% aq. NaCl (175 ml, 5 ml/g), passed through a filter agent (17.5 g, 0.5 g/g), rinsed with hexanes (35 ml, 1 ml/g), dried over MgSO$_4$ and concentrated to ~70 ml (~2 ml/g) under vacuum. To the resulting suspension was added isopropanol (IPA, 70 ml, 2 ml/g) and the solution concentrated to ~70 ml (~2 ml/g) under vacuum. The resulting suspension was stirred to afford a very thick mixture. The solids were collected via filtration and the filter cake rinsed with the liquor and IPA (35 ml, 1 ml/g). The solids were dried at 35° C. in a vacuum oven to afford bromide 15 (18.3 g, 68% yield) as an off-white solid.

$^1$H NMR (400 MHz, CDCl$_3$) δ 7.55 (s, 1H), 7.51 (s, 1H), 2.72 (s, 2H), 1.07 (S, 9H).

However, alternative reagents and reaction conditions to those disclosed above may also be employed in the de-bromination reaction. For example, reductants such as sodium borohydride, potassium borohydride, ethyl magnesium bromide, butyllithium, isopropyl magnesium chloride-lithium chloride complex, or isopropylmagnesium bromide, reduction reagents such as tetrakis(triphenylphosphine)palladium (0), iodine, palladium(II) acetate, or triphenylphosphine, solvents such as acetonitrile, diethyl ether, dimethylsulfoxide, hexane, tetrahydrofuran, or ethanol, and temperatures ranging from about −70 to about 100° C. may be employed.

iii. Preparation of Intermediate 16:

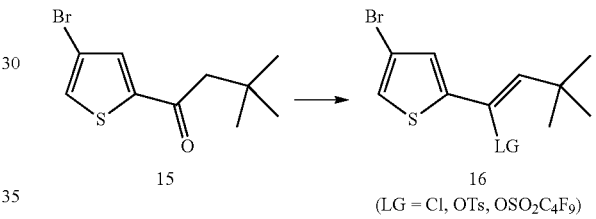

(LG = Cl, OTs, OSO$_2$C$_4$F$_9$)

Intermediate 16 (where LG=Cl) was provided from 15 according to the following procedure. A reaction vessel was charged with bromide 15 (2.61 g, 10 mmol) and isopropyl acetate (IPAc, 60 ml). The resulting solution was stirred for 10 minutes at ambient temperature and then phosphorus pentachloride (16.7 g, 80 mmol) was added. The reaction mixture was stirred at ambient temperature for 48 hours and quenched into a vigorously stirring mixture of 1M sodium carbonate solution (100 mL), ice (100 g) and IPAc (100 mL). The layers were separated and the aqueous layer extracted with IPAc (50 mL). The organic layers were combined and washed with water (100 mL), brine (100 mL) and dried over anhydrous sodium sulfate. The organic solution was concentrated in vacuo to afford a liquid (5 g). The crude product was purified by column chromatography (SiO$_2$, hexane as eluent) to afford vinyl chloride 15 (1.53 g, 55% yield) as an oil.

$^1$H NMR (400 MHz, CDCl$_3$) δ 7.12 (s, 1H), 7.07 (s, 1H), 6.19 (s, 1H), 1.26 (S, 9H).

Alternatively, 16 (where LG=OTs) was provided from 15 according to the following procedure. A reaction vessel was charged with 15 (1.31 g, 5 mmol) and THF (30 ml). The resulting solution was stirred for 10 minutes at ambient temperature and then sodium hydride (400 mg, 10 mmol, 60% oil dispersion) was added. The reaction mixture was heated to 50° C. and stirred at this temperature for 6 hours. The reaction mixture was cooled to −5° C. to 0° C. and p-toluenesulfonic anhydride (1.80 g, 5.5 mmol) was added. The reaction mixture was stirred at this temperature for 10 minutes and then warmed to ambient temperature. The reaction mixture was stirred until completion as monitored by HPLC, at which time the reaction mixture was transferred into a vigorously stirring mixture of 0.25M phosphate buffer at pH 4 (100 mL) and ice (100 g), and extracted with ethyl acetate (100 mL). The layers were separated and the aqueous layer extracted with ethyl acetate (50 mL). The combined organic layers were washed with water (100 mL), brine (100 mL) and dried over anhydrous sodium sulfate. The solvent was removed in vacuo and the residue triturated in cold hexane (50 mL). The solids were collected by filtration and dried in a vacuum oven overnight without heat to afford 4-bromo-2-(1-chloro-3,3-dimethylbut-1-enyl)thiophene (1.40 g, 67% yield) as a light tan solid.

$^1$H NMR (400 MHz, CDCl$_3$) δ 7.58 (d, 2H, J=10.8), 7.21 (d, 2H, J=10.8), 6.91 (s, 1H), 6.25 (s, 1H), 5.50 (s, 1H), 2.43 (s, 3H) 1.26 (S, 9H).

However, alternative reagents and reaction conditions to those disclosed above may also be employed. For example, reagents such as acetyl chloride, bis(trichloromethyl) carbonate, oxalyl chloride, phosphoryl chloride, zinc(II) chloride, or scandium(III) triflate, solvents such as dichloroethane, ethyl acetate, dichloromethane, or dimethylformamide, and temperatures ranging from about 20 to about 180° C. may be employed.

iv. Preparation of intermediate 9:

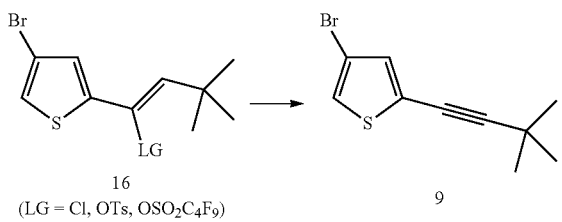

16
(LG = Cl, OTs, OSO$_2$C$_4$F$_9$)

9

Intermediate 9 was provided from 16 (where LG=Cl) according to the following procedure. A flask was charged with vinyl chloride 16 (1.05 g, 3.76 mmol) and DMF (30 ml), cooled to −5° C. to 0° C. and potassium tert-butoxide (422 mg, 3.76 mmol) was addded. The reaction was stirred at 0° C. for two hours, then warmed to ambient temperature and stirred for 1 hour. The reaction progress was monitored for completion by HPLC. If not complete, the reaction contents were cooled and fresh potassium tert-butoxide (422 mg, 3.76 mmol) was added. The mixture was stirred at 0° C. until reaction completion as monitored by HPLC. The reaction mixture was transferred into a vigorously stirring mixture of 0.25M phosphate buffer at pH 4 (100 mL) and ice (100 g), extracted with ethyl acetate (100 mL), separated, and the aqueous layer was extracted with ethyl acetate (50 mL). The combined organic layers were washed with water (3×100 mL), brine (100 mL) and then dried over anhydrous sodium sulfate. The solvent was removed in vacuo to afford a liquid (2 g). The crude product was purified by column chromatography (SiO$_2$, hexane as eluent) to afford 9 (710 mg, 78% yield) as a clear liquid.

$^1$H NMR (400 MHz, CDCl$_3$) δ 7.00 (s, 1H), 6.96 (s, 1H), 1.26 (s, 9H).

Alternatively, 9 was provided from 16 (where LG=OTs) according to the following procedure. A flask was charged with 4-bromo-2-(1-chloro-3,3-dimethylbut-1-enyl) thiophene (831 mg, 2 mmol) and toluene (30 ml). The resulting solution was stirred at ambient temperature until a solution formed. The reaction mixture was cooled to −5° C. to 0° C. and a 1N solution of lithium bis(trimethylsilyl)amide (4 mL, 4 mmol) was added dropwise. The reaction mixture was stirred at this temperature for 10 minutes and warmed to ambient temperature. The reaction was stirred until complete as monitored by HPLC, at which time the reaction mixture was poured into a vigorously stirring mixture of 0.25M phosphate buffer at pH 4 (100 mL) and ice (100 g), and extracted with toluene (100 mL). The layers were separated and the aqueous layer extracted with toluene (50 mL). The combined organic layers were washed with water (100 mL) and brine (100 mL) and dried over anhydrous sodium sulfate. The solvent was removed in vacuo and the residue purified by column chromatography (SiO$_2$, hexane as eluent) to afford 9 (240 mg, 49%) as a clear liquid.

$^1$H NMR (400 MHz, CDCl$_3$) δ 7.00 (s, 1H), 6.96 (s, 1H), 1.26 (s, 9H).

However, alternative reagents and reaction conditions to those disclosed above may also be employed to convert 16 to 9. For example, reagents such as sodium amide, indium(0), zinc(0), sodium hydride, potassium carbonate, tetrabutylammonium fluoride, sodium hydroxide, potassium hydroxide, n-butyllithium, hexamethyldisilazane, cesium carbonate, tetrabutylammonium hydroxide, potassium tert-butoxide, lithium hexamethyldisilazide, 1,8-diazabicyclo[5.4.0]undec-7-ene, potassium fluoride, alumina, cesium acetate, 18-Crown-6, sodium bicarbonate, tetrabutylammonium bisulfate, sodium methoxide, lithium diisopropylamide, tetrakis(triphenylphosphine)palladium(0), or tetrabutylammonium chloride, solvents such as ammonia, water, tetrahydrofuran, dimethylformamide, methanol, dioxane, toluene, benzene, acetonitrile, xylene, dimethylsulfoxide, tert-butanol, ethanol, diethyl ether, 2-propanol, or pyridine, and temperatures ranging from about −70 to about 138° C. may be employed.

v. Preparation of Intermediate 9 from Intermediate 15:

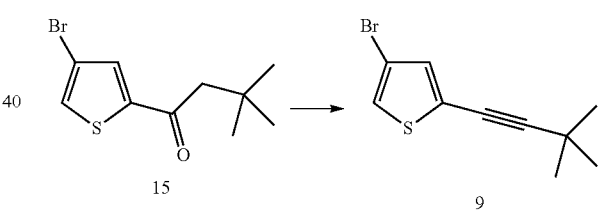

15

9

Intermediate 9 is also provided directly from 15 according to the following procedure. A flask was charged with bromide 15 (1.31 g, 5 mmol) and DMF (30 ml). The resulting solution was cooled to between −5° C. and 0° C. and perfluorobutane-1-sulfonyl fluoride (1.35 mL, 7.5 mmol) was added via syringe. The reaction mixture was stirred at this temperature for 10 minutes and tert-butylimino-tri(pyrrolidino)phosphorane (3.85 mL, 12.5 mmol) was added via syringe. The reaction was then warmed to ambient temperature, stirred until complete as monitored by HPLC, transferred to a reparatory funnel and diluted with ethyl acetate (100 mL). The solution was washed with water (100 mL) and the layers separated. The aqueous layer was extracted with ethyl acetate (50 mL). The combined organic layers were washed with water (3×100 mL) and brine (100 mL), dried over anhydrous sodium sulfate and concentrated to afford an oil (3 g). The residue was purified via column chromatography (SiO$_2$, hexane as eluent) to afford 9 (1.03 g, 84% yield) as a clear oil.

Vi. Preparation of Alternate Embodiments of Intermediate 9:

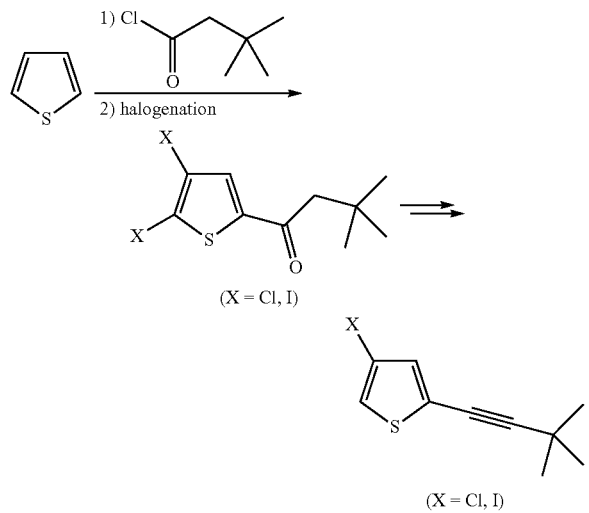

In addition to the bromide, the corresponding chloride and iodide analogs of 9 may be prepared and used in the reactions described herein. For example, the chloride analog of 14 can be prepared using a suitable chlorination reagent, such as chlorine, N-chlorosuccinimide, or sodium hypochlorite, whereas the iodide analog of 14 can be prepared using a suitable iodination reagent, such as iodine, iodic acid, or N-iodosuccinimide.

vii. Preparation of Vinyl Bromide or Vinyl Iodide as an Alternative Embodiment for Intermediate 16:

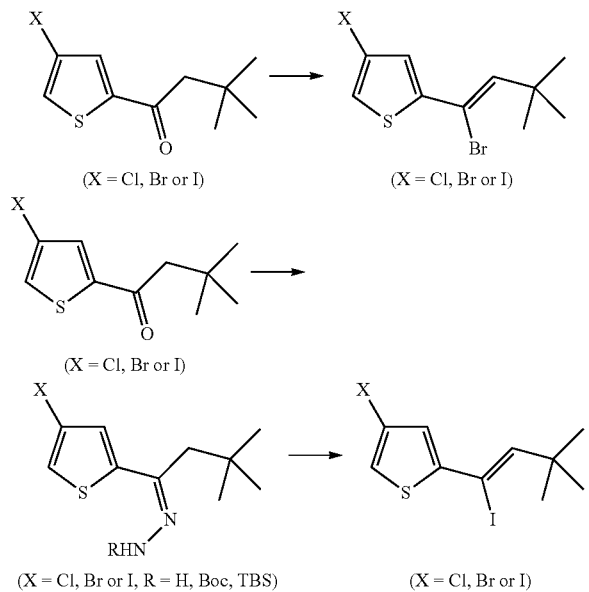

In addition to the LG groups in intermediate 16 shown above, the vinyl bromide or vinyl iodide analogs of 16 may be prepared and used in the reactions described herein. For example, the vinyl bromide can be provided using a suitable reagent, such as, phosphorous tribromide, dibromotriphenylphosphine, or dibromotriphenylphosphite. The vinyl iodide analogs of 16 may be provided from the corresponding hydrazone. The hydrazone can be prepared using a suitable regarent, such as 1,2-bis(tert-butyldimethylsilyl)-hydrazine, or hydrazine, tert-butylcarbazate. The hydrazone can then be converted to the vinyl iodide using iodine.

viii. Preparation Of Enol Sulfonates, Phosphates as Alternative Embodiments for Intermediate 16:

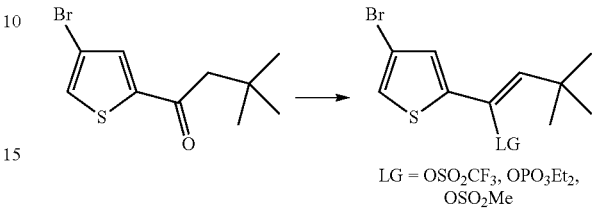

Further to the LG groups in intermediate 16 shown above, enol sulfonate and phosphate analogs of 16 may be prepared and used in the reactions described herein. For example, the enol sulfonate and phosphate analogs of 16 may be provided using a suitable base followed by an acylating agent. For example, a base such as lithium diisopropylamide, lithium hexamethyldisilazide, triethylamine, or potassium tert-butoxide, and an acylating agent such as triflic anhydride, N-phenyl bis(trifluoromethane sulfonamide), methanesulfonyl chloride, diethyl chlorophosphate may be employed.

C. Diets-Alder, and Saponification to Provide Intermediate 13:

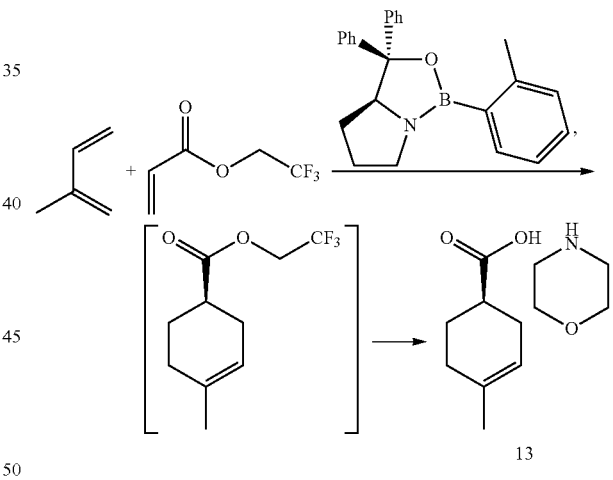

Intermediate 13 was provided using the following procedure. Charge a reactor with (S)-diphenylprolinol (1.26 kg, 0.0625 equiv) and tri-o-tolylboroxine (0.59 kg, 0.0213 equiv) and toluene (40 L). Concentrate the reactor contents at atmospheric pressure until an approximate volume of 10 L. Cool the reaction mixture to 0° C. and charge a solution of triflimide (1.11 kg, 0.05 equiv) in anhydrous DCM (7.3 L) at a rate to ensure the reaction temperature does not exceed 10° C. Charge 2,2,2-trifluoroethyl acrylate (12.2 kg, 1.0 equiv) at a rate to ensure the temperature does not exceed 10° C. Cool the mixture to 0° C. and charge isoprene (8.05 kg, 2.0 equiv) slowly over approximately 4 h maintaining a reaction temperature of 0° C. Upon reaction completion, concentrate the reaction mixture until the content of DCM is less than 20% relative to the intermediate ester. Charge tetrahydrofuran (THF, 69 L) and heat the solution to 40° C. Charge a solution lithium hydroxide monohydrate (LiOH.H₂O, 4.0 kg, 1.2 equiv) in 46 L of water over 1 h and stir until the saponification reaction is complete as determined by TLC. Concentrate the reaction mixture until less than 20 mol % THF remains relative to 13 by NMR. Charge methyl tert-butyl ether (MTBE, 50 L) and wash with water (6.1 L). Back extract the aqueous layer with MTBE (2×50 L). Discard the combined organics and concentrate product containing aqueous phase until than 5 mol % MTBE remains relative to 13. To the aqueous mixture charge heptane (46 L) and DCM (2.4 L). Wash the biphasic mixture with 4 M HCl (31 kg). Back extract the aqueous layer with n-heptane (52 L) and wash combined organics with 0.1M HCl (15 kg), and 20% brine (38 kg). To the organic solution of 13 in DCM/heptane charge morpholine (6.9 kg, 1.05 equiv) over 2 h at 20° C. Filter the resulting slurry and wash the filter cake with n-heptane (36 L). Drying the solids under vacuum at 35° C. provides 13 (98.4% ee).

$^1$H NMR (400 MHz, CDCl$_3$) δ 7.76 (s, 2H), 5.39-5.37 (m, 1H), 3.77-3.74 (m, 4H), 2.98-2.96 (m, 4H), 2.48-2.41 (m, 1H), 2.27-2.12 (m, 2H), 2.10-1.90 (m, 3H), 1.74-1.62 (m, 1H), 1.65 (s, 3H).

It is also possible, in accordance with other embodiments, to perform the enantioselective Diels-Alder reaction using a Diels-Alder catalyst derived from (S)-diphenylprolinol and tri-o-tolylboroxine with an activator such as aluminum trichloride, aluminum tribromide, or triflic acid. Alternative solvents, such as benzene, xylenes, or tetrahydrofuran; and temperatures ranging from about −45 to about 45° C. may also be employed.

In addition, alternatives to the saponification reaction may be employed. For example, sodium hydroxide or potassium hydroxide may be used with any suitable solvent, such as aqueous mixtures of methanol, isopropanol, tetrahydrofuran, or CH$_2$Cl$_2$. Acceptable temperatures can range from ambient temperature to reflux temperature of the solvent used.

The disclosure provides, in another embodiment, an alternative to the foregoing procedure to intermediate 13. The scheme below illustrates this embodiment:

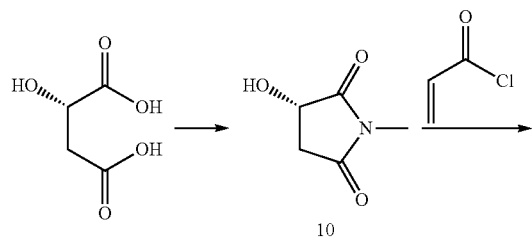

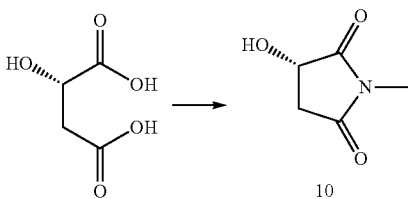

i. Cyclization to Prepare Intermediate 10:

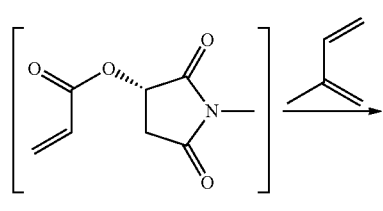

The cyclization of (S)-malic acid to provide 10 was performed using the following procedure. To a stirred solution of (S)-malic acid (10.0 kg, 1.0 equiv) in toluene (50 L) was added methyl amine (30 wt % in EtOH, 11.3 L, 1.22 equiv) in a reactor. The mixture was heated to reflux and the EtOH was removed by atmospheric distillation. The distillation was continued to azeoptropically remove the water formed in the reaction. The toluene distillate was separated from the water and returned to the reaction. Upon reaction completion, the mixture was cooled and concentrated under vacuum to a final volume of 14 L. Ethyl acetate (40 L) and silica gel (10 kg) were added to the reaction mixture and stirred at 60° C. for 18 h. The mixture was filtered and the solids were washed with 11 L of ethyl acetate. The combined organics were concentrated to 10 L and the resulting slurry was aged with agitation at 0° C. for 3 h. The mixture was filtered and the solids were washed with n-heptane (10 L). After drying the solids in an oven under vacuum, 10 was isolated (88% ee). Spectral data is consistent with commercially available 10.

Alternative reagents and reaction conditions to those disclosed above may also be employed in the cyclization reaction. For example, alternative reagents, such as methylamine solution in water, or methylamine gas, dehydrating reagents such as acetyl chloride, or acetic anhydride, alternative solvents such as xylene, tetrahydrofuran, or dichloromethane, and temperatures ranging from about 0 to about 110° C. are to be included in the present disclosure.

ii. Acylation and Diels-Alder to Prepare Intermediate 12:

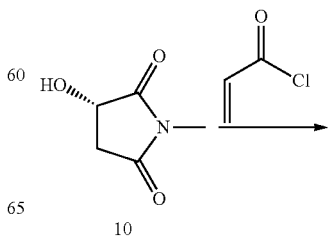

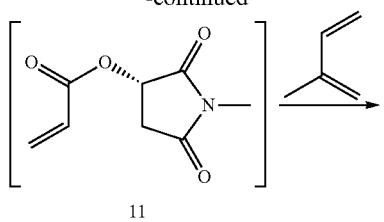

11

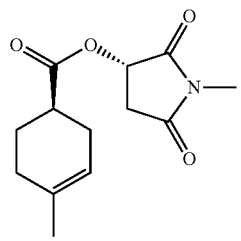

12

The acylation of 10 to provide 11, and subsequent exposure thereof to isoprene under Diels-Alder afforded 12 using the following procedure. Charge dichloromethane (DCM, 38 L) and 10 (4.81 kg, 1 equiv) to a 70 L reactor and cool the slurry to −10 to −5° C. Charge triethylamine (5.28 kg 1.4 equiv) and once the mixture becomes homogeneous, charge acryloyl chloride (3.7 kg, 1.1 equiv) to the reactor at a rate to ensure that the reaction temperature does not exceed −5° C. Upon reaction completion, wash the reaction with 1 N HCl (20 kg) and allow the mixture to warm to ambient temperature. The organics are washed with 5% NaHCO$_3$ (24.3 kg) and 5% brine (23.8 kg). Dry the resulting organic phase with Na$_2$SO$_4$ (5.5 kg), filter the solids, and wash the filter cake with hexanes (8 L) to provide 11 in solution. Charge an appropriate amount of DCM (12 L) to this solution in order to achieve a final volume of 51 L. Split this mixture evenly between two reactors and cool the contents of the reactors to −10° C. Charge TiCl$_4$ (1 M in DCM, 4.4 kg, 0.24 equiv) to each reactor at a rate to ensure the temperature does not exceed −9° C. Charge isoprene (7.25 kg, 5.8 equiv) to the resulting slurry in each reactor. Stir the mixtures at −10° C. until the reaction is complete. Charge solid Na$_2$CO$_3$*10H$_2$O (2.26 kg) to each reaction mixture and warm the reactors' contents to 23° C. Stir for a NLT 2 h and filter the reaction mixtures in separate filters. Rinse the two filter cakes with DCM (2 L each) and wash the combined filtrate and rinses from each filtration with water (20 L each). Dry each organic mixture with Na$_2$SO$_4$ (2.6 kg each) and filter off the solids. Rinse the filter cakes with an appropriate amount of DCM. Separately concentrate both 12 containing DCM solutions to an oil. Return each concentrated oil to separate clean reactors and charge 7 volumes of methyl tert-butyl ether (MTBE, 30.8 L and 29.5 L, respectively) and heat the mixtures to 55° C. The following operations were performed separately for each solution: Charge 4 volumes of heptanes (17.6 L and 16.5 L, respectively) and allow mixture to return to 55° C. Ensure the solvent ratio is appropriate by $^1$H-NMR, if not then adjust. Filter the resulting fine slurry and gummy solids while at 55° C. and concentrate the resulting filtrate. Dissolve the resulting solids in 5 vol of isopropanol (IPA, 23 L and 20 L, respectively) at 45° C. and cool to −3 to 15° C. over 3 h and age slurry for 18 h. Filter the resulting slurry and rinse with a minimum volume of cold IPA. Dry the resulting solids in an oven at 40° C. under vacuum to provide 12 (96:4 dr).

$^1$H NMR (400 MHz, CDCl$_3$) δ 5.46 (dd, J=8.7, 4.7 Hz, 1H), 5.36 (s, 1H), 3.16 (dd, J=18.3, 8.7 Hz, 1H), 3.05 (s, 3H), 2.64 (dd, J=18.3, 4.7 Hz, 1H), 2.54-2.64 (m, 1H), 2.24 (br. s, 2H), 2.02 (br. s, 3H), 1.69-1.82 (m, 1H), 1.65 (s, 3H).

Alternative reagents and/or reaction conditions to those disclosed above are to be included in the present disclosure.

Acceptable alternatives for the acylation step include solvents, such as tetrahydrofuran, chloroform, or dimethylormamide, bases, such as disopropylethylamine, dimethylaminopyridine, or imidazole, and temperatures ranging from about −48 to about 35° C.

Acceptable alternatives for the Diels-Alder step includes catalysts, such as Et$_2$AlCl, aluminum trichloride THF complex, tin tetrachloride, TiCl$_2$(OiPr)$_2$, and complexes of TiCl$_4$ with (R,R)-hydrobenzoin, and/or (S,S)-hydrobenzoin, solvents, such as toluene, mesitlyene, or xylenes, and temperatures ranging from about −48 to about 35° C.

iii. Saponification to Prepare Intermediate 13:

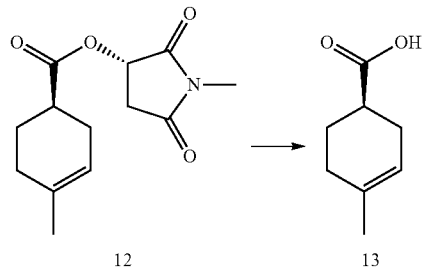

12       13

The saponification of 12 to provide 13 was performed using the following procedure. Charge a 12 (3.0 kg, 1.0 equiv) solution in tetrahydrofuran (THF, 34 L) to a 70 L reactor. Charge the reactor with water (27 L) and lithium hydroxide monohydrate (2.51 kg, 5 equiv) and stir the biphasic mixture at 20 to 27° C. until the reaction is complete. Concentrate the completed reaction to remove the THF and with stirring adjust the pH of the resulting aqueous mixture to 1-2 by adding 5 N HCl (40 L). Extract the acidic solution with a 98:2 mixture of hexanes:dichloromethane (25 L). Back extract the aqueous layer with 98:2 mixture of hexanes:dichloromethane (12.2 L) and dry the combined organics with sodium sulfate (1.7 kg). Filter off solids and rinse the filter cake with a 1:1 mixture of hexanes:dichloromethane (10 L). Concentrate the combined organics to dryness and continue drying the resulting solids in an oven at 40° C. under vacuum to afford 13 (90% ee).

$^1$H NMR (400 MHz, CDCl$_3$) δ 5.46-5.31 (m, 1H), 2.48-2.60 (m, 1H), 2.15-2.33 (m, 2H), 2.11-1.92 (m, 3H), 1.82-1.62 (m, 1H), 1.66 (s, 3H).

However, alternative reagents and reaction conditions to those disclosed above may also be employed. For example, in certain alternative embodiments, the saponification reaction above can employ dehydrating reagents, such as acetyl chloride, or acetic anhydride, a solvent selected from xylenes, and methanol, and/or a temperature from about 0 to about 110° C.

Further to the above processes for obtaining 13, in some embodiments, the enantiopurity of 13 can be increased by chiral resolution. Such methods are well known in the art.

II. Synthesis of 5-(3,3-Dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (I)

A. N-Arylation, Acylation, and Carboxylation to Provide Formula I:

i. N-Arylation to Prepare 5-(3,3-dimethylbutyn-1-yl)-3-[(cis-4-hydroxy-4-{[(3S)-tetrahydrofuran-3-yloxy]methyl}cyclohexyl)amino]thiophene (III)

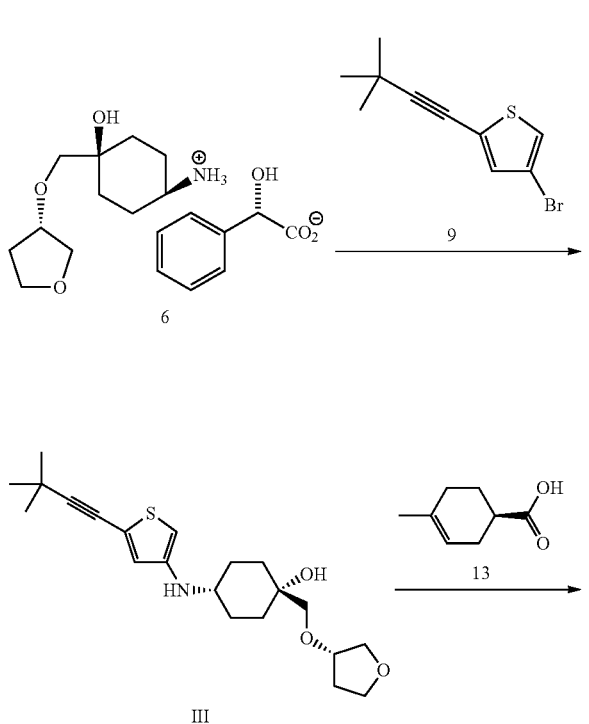

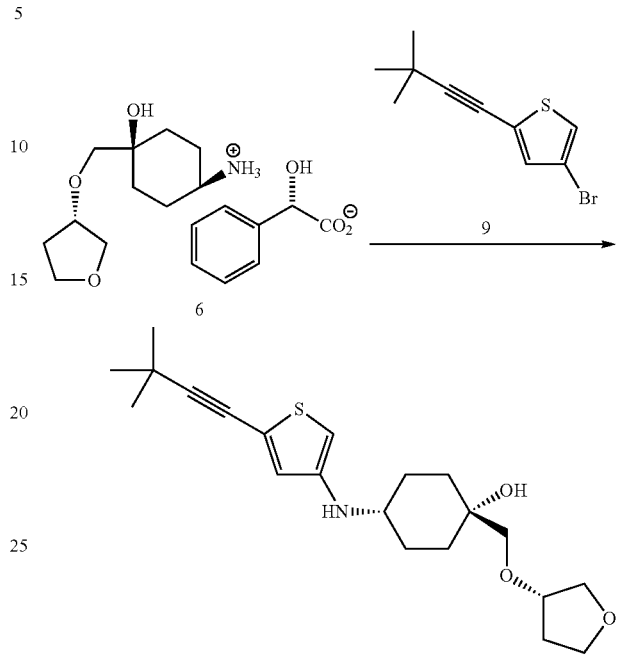

The N-arylation reaction to provide III was performed using the following procedure. Charge a 125-mL reaction vessel with Pd$_2$(dba)$_3$ (57 mg, 0.3 mol %), t-Bu-BippyPhos (0.63 g, 7 mol %), and KOH (3.5 g, 3.0 equiv). Inert the vessel and charge t-amylalcohol (40 mL, 8 vol), water (2 mL, 0.4 vol), 6 (9.1 g, 1.2 equiv), and 9 (5.0 g, 1.0 equiv). Inert vessel and heat reactor contents to 90° C. until the reaction is complete. Cool reaction mixture to 23° C. and concentrate mixture under reduced pressure to give brown solids. Purify crude solids by silica gel chromatography in EtOAc to provide III as a tan solid (99.9:0.1 diastereomeric ratio by achiral HPLC).

$^1$H NMR (400 MHz, CDCl$_3$) δ 6.60 (d, J=2.0 Hz, 1H), 5.78 (d, J=2.0 Hz, 1H), 4.16-4.10 (m, 1H), 3.88 (dd, J=16.6, 7.9 Hz, 1H), 3.84-3.76 (m, 3H), 3.25 (dd, J=19.2, 8.7 Hz, 2H), 3.09-2.98 (m, 1H), 2.01-1.95 (m, 2H), 1.94-1.90 (m, 2H), 1.77-1.74 (m, 2H), 1.59-1.44 (m, 2H), 1.42-1.31 (m, 2H), 1.29-1.27 (m, 9H).

Alternatives to the N-arylation reagents and reaction conditions disclosed above are to be included in the present disclosure.

For example, the N-arylation catalyst can be any suitable palladium, platinum, or copper based catalyst catalyst, such as copper(I) chloride, tris(dibenzylideneacetone)dipalladium (0), copper(II) chloride, copper(I) bromide, copper(II) bromide, copper(I) acetate, copper(II) acetate, copper(II) acetylacetonate, copper(I) trifluoromethanesulfonate, copper(II) trifluoromethanesulfonate, copper(I) thiophene-2-carboxylate, or copper(I) iodide. Any suitable ligand may be employed, such as 5-(di-tert-butylphosphino)-1',3',5'-triphenyl-1'H-[1,4]bipyrazole, 2-(di-tert-butyl-phosphino)-1-phenyl-1H-pyrrole, 2-(di-tert-butylphosphino)-1-(2-methoxyphenyl)-1H-pyrrole, acetylacetone, acetylcyclohexanone, isobutyrylcyclohexanone, N$^1$,N$^2$-dimethylcyclohexane-1,2-diamine, L-proline, BINAP, or N,N-diethylsalicylamide.

In some embodiments, other suitable bases are used. These include potassium hydroxide, sodium hydroxide, sodium tert-amylate, cesium carbonate, cesium hydroxide, potassium phosphate tribasic, sodium tertbutoxide, sodium methoxide, or sodium ethoxide. Any suitable solvent may be employed, such as toluene, water, acetonitrile, dimethylformamide, N-methylpyrrolidinone, or 2-methyl-THF. Suitable temperatures for carrying out the reaction range from about 50 to about 110° C.

ii. Acylation to Provide 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene (IV)

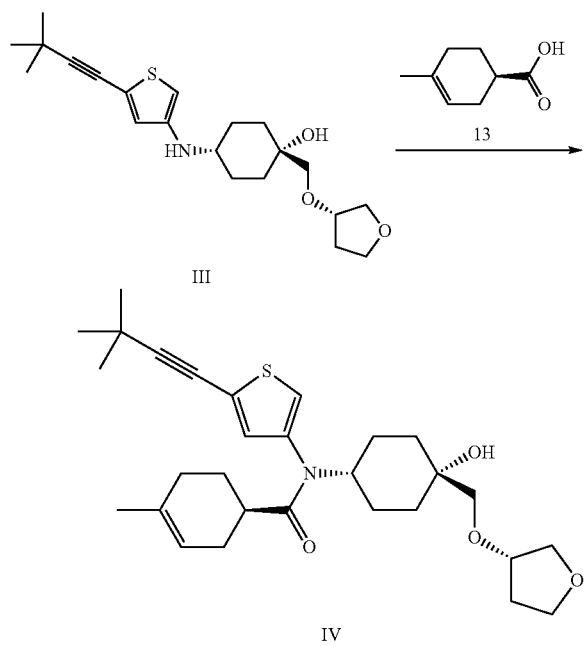

Acylation of III to provide IV was performed using the following procedure. A 15-mL flask equipped with a magnetic stir bar and a nitrogen inlet was charged with 13 (557 mg, 1.5 equiv), 2-methyl-THF (5 mL) and a drop of DMF (ca. 2 µL). The reaction mixture was cooled to 4° C. using an ice bath. To the reaction mixture was added oxalyl chloride (0.32 mL, 1.4 equiv) dropwise over 1 min. The reaction mixture was allowed to warm to 19° C. over 30 min and aged at 19° C. for 3 h. To a 50-mL flask equipped with a magnetic stir bar and a nitrogen inlet were added III (1.00 g, 1.0 equiv), 2-methyl-THF (5 mL) and diisopropylethylamine (1.38 mL, 3 equiv), and the contents were cooled to 7° C. using an ice bath. To the slurry of III was added the solution of the acid chloride dropwise over 5 min. The reaction mixture was allowed to warm to 17° C. over 30 min and aged for 3 h. The reaction mixture was quenched with 10 wt % aqueous citric acid (10 mL) and the phases were separated. The organic phase was washed with water (10 mL) and concentrated under reduced pressure. The residue was dissolved in isopropanol (25 mL) and concentrated to ca. 5 mL. To the solution was added water (5 mL) over 10 min and seed crystal of IV (5 mg, 0.5 wt %). The slurry was aged at room temperature for 16 h and filtered. The filter cake was rinsed with 1/1 iPA/water (6 mL) and dried in a vacuum oven for 24 h to afford IV.

$^1$H NMR (400 MHz, CDCl$_3$) δ 6.86 (d, J=1.8 Hz, 1H), 6.82 (d, J=1.8 Hz, 1H), 5.30-5.25 (m, 1H), 4.55-4.45 (m, 1H), 4.15-4.03 (m, 2H), 3.89-3.72 (m, 4H), 3.32-3.20 (m, 2H), 2.30-2.18 (m, 2H), 1.99-1.67 (m, 11H), 1.56-1.36 (m, 4H), 1.34-1.30 (m, 9H).

Alternatives to the acylation reagents and reaction conditions disclosed above may also be employed.

For example, the halogenating reagent can be any suitable halogenating reagent, such as oxalyl chloride, thionyl chloride, phosphorous oxychloride, chlorotripyrrolidinophosphonium hexafluorophosphate, triethylamine, imidazole, or 1,8-bis(dimethylamino)naphthalene. Furthermore, the halogenation of 13 can be performed in situ, as described hereinabove, or in a separate vessel prior to reacting with III.

Any suitable solvent can be employed, such as 2-methyl-THF, methyl tert-butyl ether, cyclopentyl methyl ether, or dichloromethane, and the temperature can range from about −45 to about 100° C.

The acylation reaction conditions can comprise any suitable base, such as imidazole, pyridine, N,N-diisopropylethylamine, or 2,2,6,6-tetramethylpiperidine.

In addition, the acylation of III with 13 can be performed under standard peptide coupling conditions, which conditions are well known in the art. For example, coupling reagents such as 1,1'-carbonyldiimidazole, dicyclohexylcarbodiimide, diisopropylcarbodiimide, 1-hydroxy-benzotriazole, 1-hydroxy-7-aza-benzotriazole, ethyl 2-cyano-2-(hydroxyimino)acetate, O-(7-azabenzotriazol-1-yl)-N,N,N',N'-tetramethyluronium hexafluorophosphate, benzotriazole-1-yl-oxy-tris-(dimethylamino)-phosphonium hexafluorophosphate, or benzotriazol-1-yl-oxytripyrrolidinophosphonium hexafluorophosphate can be used to activate 13 prior to contacting with III.

iii. Carboxylation to provide 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid (I)

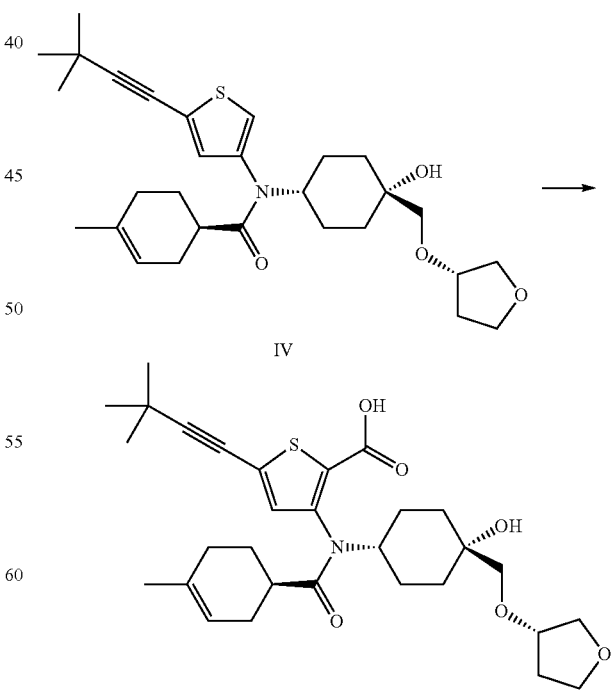

Carboxylation of IV to provide I was performed using the following procedure. In a 50 mL flask, IV (1.00 g, 1.0 equiv) and THF (10 mL) were placed, and the solution was cooled to −11° C. using acetone/ice bath. To the solution was added n-BuLi (2.4 mL, 2.5 M solution in hexanes, 3 equiv) over 10 min maintaining internal temperature below −3° C. The reaction mixture was allowed to age between −12° C. to −10° C. for 1 h. Carbon dioxide (lecture bottle equipped with a pressure regulator) was introduced through a needle, and the bubbling was continued for 10 min. The reaction mixture was aged at −10° C. for 1 h, quenched with 10 wt % aqueous citric acid (10 mL) and allowed to warm to 19° C. The layers were separated and the organic solution was diluted with isopropyl acetate (50 mL). The solution was concentrated to ca. 5 mL under reduced pressure. To the solution was then added benzylamine (0.22 mL, 1 equiv). The slurry was aged for 30 min, and filtered. The filter cake was rinsed with iPAc (10 mL). In a 50 mL flask were added the wet cake of I, iPAc (10 mL) and 10 wt % aqueous citric acid (10 mL). The mixture was stirred until all solids dissolved, and the phases were separated. The organic phase was washed with water (10 mL), and diluted with iPAc (50 mL). The solution was concentrated to ca. 5 mL and added seed crystal of I (5 mg, 0.5 wt %). To the slurry was added heptane (10 mL) over 2 h, and the slurry was filtered. The filter cake was washed with 2/1 heptane/iPAc (6 mL) and dried in vacuum oven. Note: Slow interconversion between two rotamers on NMR timescale gives rise to two sets of NMR signals.

$^1$H NMR (400 MHz, DMSO-d6) δ 13.48 (br. s., 1H), 7.21, s; 7.16, s, (1H), 5.28, m; 5.24, m, (1H); 4.32 (m, 1H); 4.06 (m, 1H); 3.99 (br. s, 1H); 3.70 (dd, J=8.0, 15.2 Hz, 1H); 3.65 (ddd J=8.0, 15.2, 3.2 Hz, 1H); 3.63 (m, 2H), 3.10 (dd, J=9.6, 1.6 Hz, 1H), 3.06 (d, J=9.6 Hz, 1H), 2.20, m; 2.09, m, (1H); 2.05, m; 1.90, m, (1H); 1.86 (m, 2H); 1.86, m; 1.82, m, (1H); 1.80, m; 1.76, m, (1H); 1.70, m; 1.64, m (1H); 1.68, m; 1.63, m (1H); 1.55, m; 1.38, m (1H); 1.54, m; 1.42, m (2H); 1.52 (s, 3H); 1.48, m; 1.16, m (2H); 1.46 (m, 2H); 1.42 (m, 2H); 1.30, s, 1.29, s (9H).

However, alternative reagents and/or reaction conditions to those disclosed above may also be employed in the carboxylation reaction. For example, other acceptable bases, such as sodium hydride, potassium hydride, sodium hexamethyldisilazine, n-butyl lithium, n-hexyl lithium, phenyl lithium, ethyl lithium, lithium tetramethylpiperidide, or lithium diisopropylamide, can be employed. Alternative solvents may also be used, such as diethylether, or methyl tertbutyl ether, and any suitable temperature ranging from about −78 to about 45° C., may be used in the process described above. In some embodiments, compounds of Formula I can be further purified via crystallization with cinchona alkaloids

We claim:

1. A process for the preparation of a compound of Formula I:

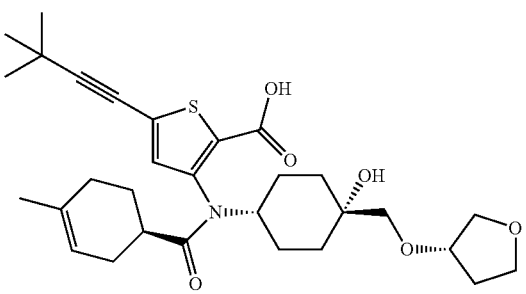

(I)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene-2-carboxylic acid, or a stereoisomer, mixture of stereoisomers, pharmaceutically acceptable salt or ester thereof, comprising:

contacting a compound of Formula IV, named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof, with a base in the presence of $CO_2$:

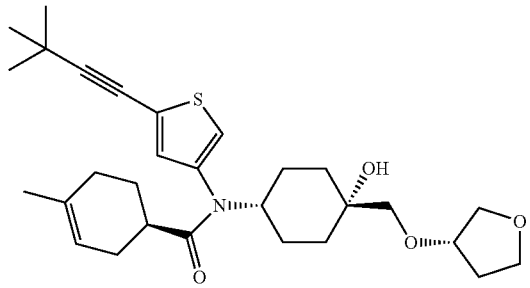

(IV)

under carboxylation reaction conditions to provide the compound of Formula I or a stereoisomer, mixture of stereoisomers, pharmaceutically acceptable salt or ester thereof.

2. A process for the preparation of a compound of Formula IV:

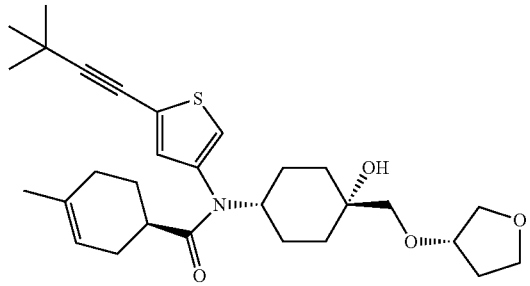

(IV)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof, comprising contacting a compound of Formula III, named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof, with a compound of Formula XI or a stereoisomer, or mixture of stereoisomers thereof:

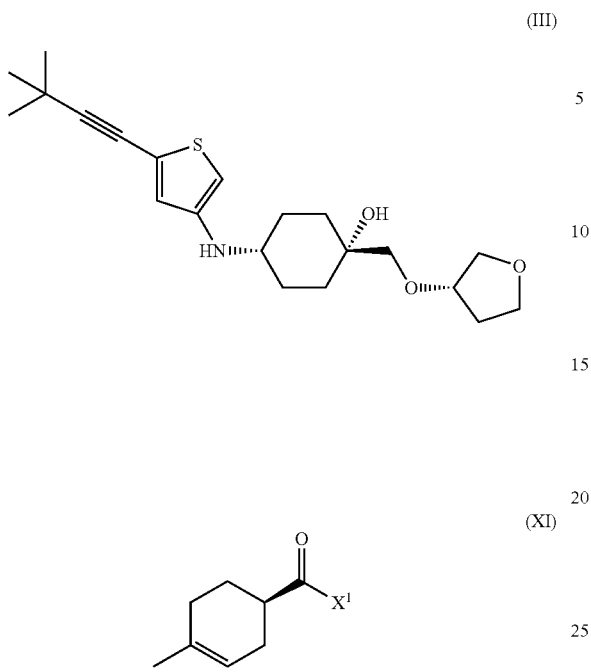

(III)

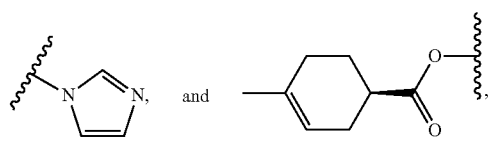

(XI)

wherein:
X[1] is selected from the group consisting of halogen,

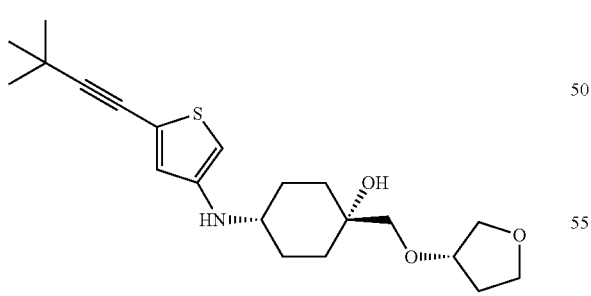

under acylation reaction conditions to provide the compound of Formula IV or a stereoisomer, mixture of stereoisomers, or salt thereof.

3. A process for the preparation of a compound of Formula III:

(III)

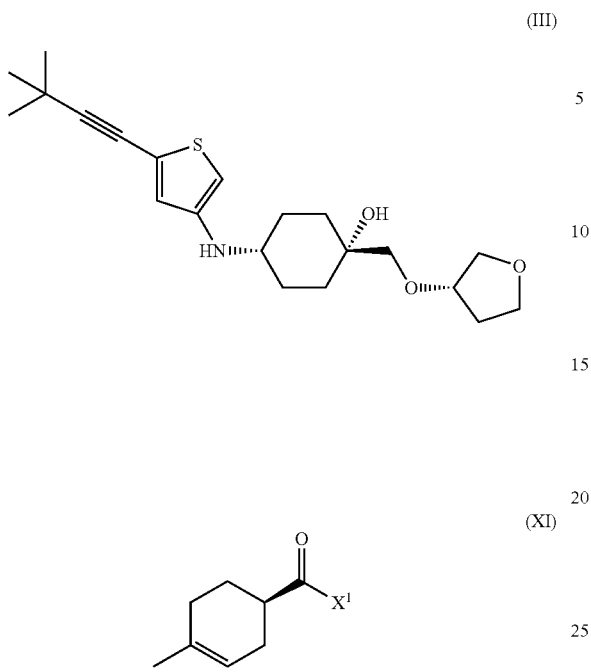

named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof, comprising contacting a compound of Formula II, named (cis-4-hydroxy-4-{[(3S)-tetrahydrofuran-3-yloxy]methyl}cyclohexyl)amine, or a stereoisomer, mixture of stereoisomers, or salt thereof, with a compound of Formula X:

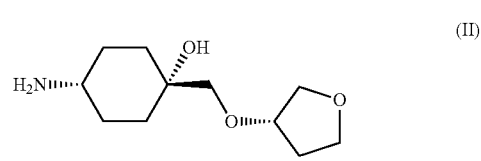

(II)

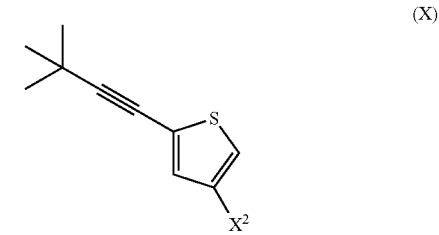

(X)

wherein:
X[2] is selected from the group consisting of halogen, triflate, and —B(OY)$_2$, wherein each Y is independently H or C$_{1-4}$ alkyl, or two Y groups together with the atoms to which they are attached form a 5- to 6-membered ring, under N-arylation reaction conditions to provide the compound of Formula III or a stereoisomer, mixture of stereoisomers, or salt thereof.

4. A process for the preparation of a compound of Formula I:

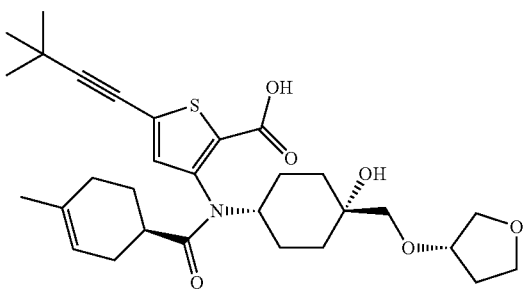

(I)

or a stereoisomer, mixture of stereoisomers, pharmaceutically acceptable salt or ester or thereof, comprising the steps of:

a) contacting a compound of Formula II, named (cis-4-hydroxy-4-{[(3S)-tetrahydrofuran-3-yloxy]methyl}cyclohexyl)amine, or a stereoisomer, mixture of stereoisomers, or salt thereof, with a compound of Formula X:

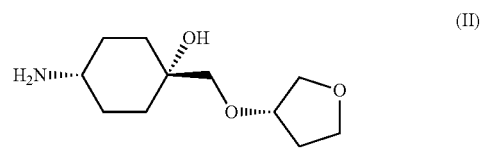

(II)

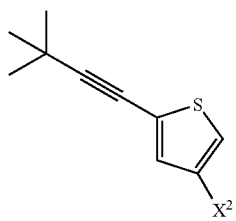
(X)

wherein:
X² is selected from the group consisting of halogen, triflate, and —B(OY)₂, wherein each Y is independently H or C₁₋₄ alkyl, or two Y groups together with the atoms to which they are attached form a 5- to 6-membered ring, under N-arylation reaction conditions to provide the compound of Formula III, named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof;

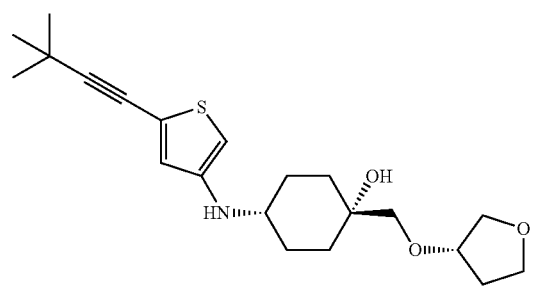
(III)

b) contacting a compound of Formula III or a stereoisomer, mixture of stereoisomers, or salt thereof, with a compound of Formula XI or a stereoisomer, or mixture of stereoisomers thereof:

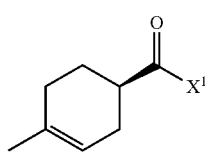
(XI)

wherein:
X¹ is selected from the group consisting of halogen,

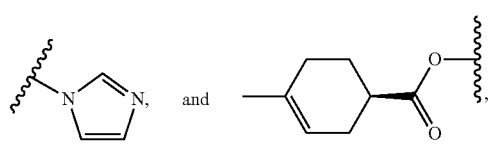 [SMILES: *n1ccnc1 ; "and" ; *OC(=O)[C@H]1CC=C(C)CC1 ; ","]

under acylation reaction conditions to provide the compound of Formula IV, named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof;

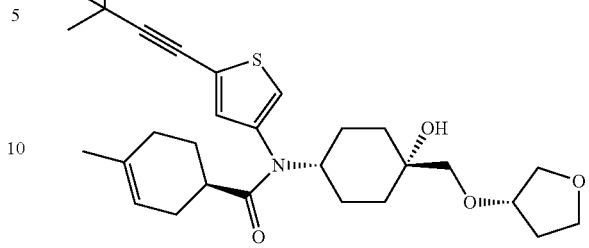
(IV)

c) contacting a compound of Formula IV or a stereoisomer, mixture of stereoisomers, or salt thereof, with a base in the presence of $CO_2$ under carboxylation reaction conditions to provide the compound of Formula I or a stereoisomer, mixture of stereoisomers, pharmaceutically acceptable salt or ester thereof.

5. The process of claim 3, wherein the N-arylation reaction conditions comprise a catalyst.

6. The process of claim 5, wherein the catalyst is a palladium, platinum, or copper based catalyst.

7. The process of claim 6, wherein the catalyst is selected from the group consisting of tris(dibenzylideneacetone)dipalladium(0), copper(I) chloride, copper(II) chloride, copper(I) bromide, copper(II) bromide, copper(I) acetate, copper(II) acetate, copper(II) acetylacetonate, copper(I) trifluoromethanesulfonate, copper(II) trifluoromethanesulfonate, copper(I) thiophene-2-carboxylate, and copper(I) iodide.

8. The process of claim 3, wherein the N-arylation reaction conditions further comprise a ligand.

9. The process of claim 8, wherein the ligand is selected from the group consisting of 5-(di-tert-butylphosphino)-1',3',5'-triphenyl-1'H-[1,4]bipyrazole, 2-(di-tert-butyl-phosphino)-1-phenyl-1H-pyrrole, 2-(di-tert-butylphosphino)-1-(2-methoxyphenyl)-1H-pyrrole, acetylacetone, acetylcyclohexanone, isobutyrylcyclohexanone, $N^1,N^2$-dimethylcyclohexane-1,2-diamine, L-proline, BINAP, and N,N-diethylsalicylamide.

10. The process of claim 3, wherein the N-arylation reaction conditions comprise a base.

11. The process of claim 10, wherein the base is selected from the group consisting of potassium hydroxide, sodium hydroxide, sodium tert-amylate, cesium carbonate, cesium hydroxide, potassium phosphate tribasic, sodium tertbutoxide, sodium methoxide, and sodium ethoxide.

12. The process of claim 3, wherein the N-arylation reaction conditions comprise a phase transfer catalyst.

13. The process of claim 12, wherein the phase transfer catalyst is cetyltrimethyl ammonium bromide.

14. The process of claim 3, wherein the compound of Formula II is the free base.

15. The process of claim 3, wherein the compound of Formula II is a salt.

16. The process of claim 15, wherein the compound of Formula II is the hydrochloric acid salt or the (S)-mandelic acid salt.

17. The process of claim 2, wherein the acylation reaction conditions comprise a base.

18. The process of claim 17, wherein the base is imidazole, pyridine, N,N-diisopropylethylamine, or 2,2,6,6-tetramethylpiperidine.

19. The process of claim 2, wherein the acylation reaction temperature conditions are about −45 °C. to about 45 °C.

20. The process of claim 19, wherein the acylation reaction temperature conditions are about 0 ° C. to about 20 ° C.

21. The process of claim 1, wherein the carboxylation reaction conditions comprise about a three-fold equivalent of the base.

22. The process of claim 21, wherein the base is selected from the group consisting of sodium hydride, potassium hydride, sodium hexamethyldisilazine, n-butyl lithium, n-hexyl lithium, phenyl lithium, ethyl lithium, lithium tetramethylpiperidide, and lithium diisopropylamide.

23. The process of claim 1, wherein the carboxylation reaction temperature conditions are from about −78 ° C. to about 45 ° C.

24. The process of claim 23, wherein the carboxylation reaction temperature conditions are from about −20 ° C. to about 20 ° C.

25. A compound of Formula III:

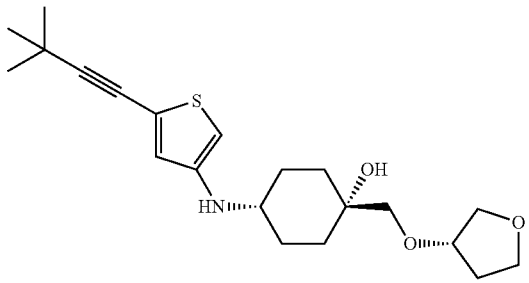

(III)

named 5-(3,3-dimethylbutyn-1-yl)-3-[(cis-4-hydroxy-4-{[(3S)-tetrahydrofuran-3-yloxy]methyl}cyclohexyl)amino]thiophene, or a stereoisomer, mixture of stereoisomers, or salt thereof.

26. A compound of Formula IV:

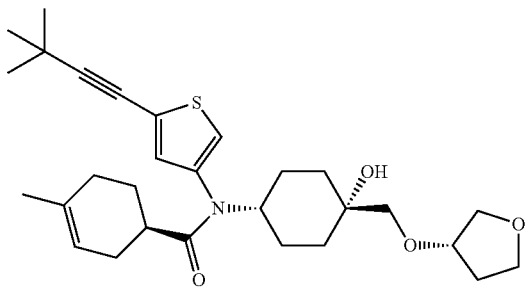

(IV)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene, or a stereoisomer, mixture of stereoisomers, or salt thereof.

27. A compound of Formula V:

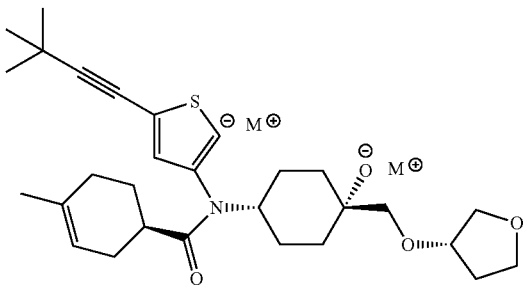

(V)

named 5-(3,3-dimethylbutyn-1-yl)-3-[(cis-4-hydroxy-4-{[(3S)-tetrahydrofuran-3-yloxy]methyl}cyclohexyl){[(1R)-4-methylcyclohex-3-en-1-yl]carbonyl}amino]thiophene metal salt, or a stereoisomer or mixture of stereoisomers thereof, wherein each M is independently a metal.

28. The compound of claim 27, wherein M is lithium.

29. A compound of Formula II:

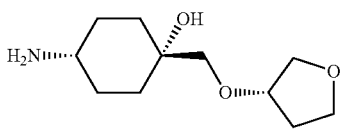

(II)

named (cis-4-hydroxy-4-{[(3S)-tetrahydrofuran-3-yloxy]methyl}cyclohexyl)amine, or a stereoisomer, mixture of stereoisomers, or salt thereof.

30. The compound of claim 29, wherein the compound of Formula II is a free base.

31. The compound of claim 29, wherein the compound of Formula II is a salt.

32. The compound of claim 31, wherein the compound of Formula II is the hydrochloric acid salt or the (S)-mandelic acid salt.

* * * * *

UNITED STATES PATENT AND TRADEMARK OFFICE
CERTIFICATE OF CORRECTION

PATENT NO. : 8,759,544 B2
APPLICATION NO. : 13/801039
DATED : June 24, 2014
INVENTOR(S) : Jared Wayne Evans et al.

It is certified that error appears in the above-identified patent and that said Letters Patent is hereby corrected as shown below:

Title page 2
In Other Publications Item (56)

U.S. Appl. No. 13/800,991, filed Mar. 13, 2013, delete "Hashah" et al., and insert -- Hashash --

In the specification

Column 4, line 18, delete "ofhalogen" and insert -- of halogen --

In the claims

Claim 3, column 52, line 25, delete "ofhalogen" and insert -- of halogen --

Claim 4, column 53, line 14, delete "ofhalogen" and insert -- of halogen --

Claim 9, column 54, lines 36-39, delete "5-(di-tert-butylphosphino)-1',3',5'-triphenyl-1'H-[1,4]bipyrazole, 2-(di-tert-butyl-phosphino)-1-phenyl-1H-pyrrole, 2-(di-tert-butylphosphino)-1-(2-methoxyphenyl)-1H-pyrrole," and insert -- 5-(di-tert-butylphosphino)-1',3',5'-triphenyl-1'H-[1-4']bipyrazole, 2-(di-tert-butyl-phosphino)-1-phenyl-1H-pyrrole, 2-(di-tert-butylphosphino)-1-(2-methoxyphenyl)-1H-pyrrole, --

Claim 9, column 54, line 40, delete "N$^1$,N$^2$-dimethylcyclohexane-1,2-diamine," and insert -- $N^1,N^2$-dimethylcyclohexane-1,2-diamine, --

Claim 9, column 54, line 41, delete "N,N-diethylsalicylamide." and insert -- $N,N$-diethylsalicylamide. --

Signed and Sealed this
Thirtieth Day of September, 2014

Michelle K. Lee
*Deputy Director of the United States Patent and Trademark Office*

CERTIFICATE OF CORRECTION (continued)
U.S. Pat. No. 8,759,544 B2

Claim 19, column 54, line 67, delete "-45° C." and insert -- -45° C --

Claim 20, column 55, line 2, delete "0° C." and insert -- 0° C --

Claim 23, column 55, line 12, delete "-78° C." and insert -- -78° C --

Claim 24, column 55, line 15, delete "-20° C." and insert -- -20° C --